(12) United States Patent
Favre et al.

(10) Patent No.: US 6,613,321 B1
(45) Date of Patent: *Sep. 2, 2003

(54) LIVE VACCINES AGAINST GRAM-NEGATIVE PATHOGENS, EXPRESSING HETEROLOGOUS O-ANTIGENS

(75) Inventors: Didier Favre, Dudingen (CH); Stanley J. Cryz, Neuenegg (CH); Jean-Francois Viret, Laupen (CH)

(73) Assignee: Swiss Serum and Vaccine Institute Berne, Berne (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/051,536
(22) PCT Filed: Oct. 4, 1996
(86) PCT No.: PCT/EP96/04334
§ 371 (c)(1),
(2), (4) Date: Jun. 15, 1998
(87) PCT Pub. No.: WO97/14782
PCT Pub. Date: Apr. 24, 1997

(30) Foreign Application Priority Data
Oct. 13, 1995 (EP) .............................. 95116208

(51) Int. Cl.⁷ ...................... A61K 38/54; A61K 39/106; A61K 39/112; A61K 39/108; A61K 39/02
(52) U.S. Cl. ................ 424/93.4; 424/184.1; 424/261.1; 424/258.1; 424/257.1; 424/234.1; 424/200.1
(58) Field of Search ......................... 424/184.1, 200.1, 424/236.1, 93.4, 93.2, 241.1, 257.1, 258.1, 261.1; 514/54, 837, 867

(56) References Cited
U.S. PATENT DOCUMENTS 5,066,596 A * 11/1991 Manning et al. ........ 435/252.33
5,110,588 A * 5/1992 Morona et al. ............... 424/92

FOREIGN PATENT DOCUMENTS

EP 0 564 689 * 10/1993
WO WO 94/01562 * 1/1994

OTHER PUBLICATIONS

Manning et al. In: Vibrio cholerae and Cholera: Molecular to Global Perspectives. (Ed) Wachsmuth et al. American Society for Microbiology, ASM Press, Washington, Chapter 6, pp. 77–94, 1994.*
Morona et al. FEMS Microbiol. Lett. 82: 279–286, 1991.*
Manning et al. Infect. Immun. 53: 272–277, 1986.*
Viret et al. Mol. Microbiol. 7: 239–252, 1993.*
Newland et al. Vaccine 10: 766–776, 1992.*
Forrest. Infect. Immun. 60: 2023–2029, 1992.*
Kotloff et al. Infect. Immun. 60: 2218–2224, 1992.*
Attridge et al. Infect. Immun. 59: 2279–2284, 1991.*
Falt et al. J. Bacteriol. 177: 5310–5315, Sep., 1995.*
Viret et al. Biologicals 22: 361–372, 1994.*
Cheah et al. FEMS Microbiol. Lett. 67: 213–218, Oct., abstract, 1991.*
Smirnova et al. Microb. Pathog. 19: 65–72, Aug., abstract, 1995.*
Seltmann et al. Int. J. Med. Microbiol. Virol. Parasitol. Infect. Dis. 277: 419–428, abstract, 1992.*
Kotloff et al. 15: 495–502, Apr., abstract, 1995.*
Forrest et al. Vaccine 9: 515–520, abstract, 1991.*
Falt et al. Eur. J. Biochem. 213: 573–581, abstract, 1993.*
Goldberg et al. Proc. Natl. Acad. Sci. USA 89: 10716–10720, abstract, 1992.*

* cited by examiner

*Primary Examiner*—S. Devi
(74) *Attorney, Agent, or Firm*—Birch, Stewart, Kolasch & Birch, LLP

(57) ABSTRACT

The present invention relates to live attenuated gram-negative vaccine carrier strains which are useful for expression and delivery of heterologous O-antigens (O-PS) from gram-negative pathogens. Said strains are deficient in the expression of homologous O-PS due to a defined genetic modification, preferably a deletion, and, thus, capable of efficiently expressing a desired heterologous O-PS in such a way that it is covalently coupled either to homologous or heterologous LPS core lipid A. The present invention furthermore relates to live vaccine carrier strains containing a heterologous gene or a set of heterologous genes encoding O-PS. Preferably, said strains additionally contain genes necessary for the synthesis of complete smooth heterologous LPS. The present invention also relates to live vaccines comprising said strains, preferably for immunization against gram-negative enteric pathogens.

23 Claims, 13 Drawing Sheets

Figure 1:
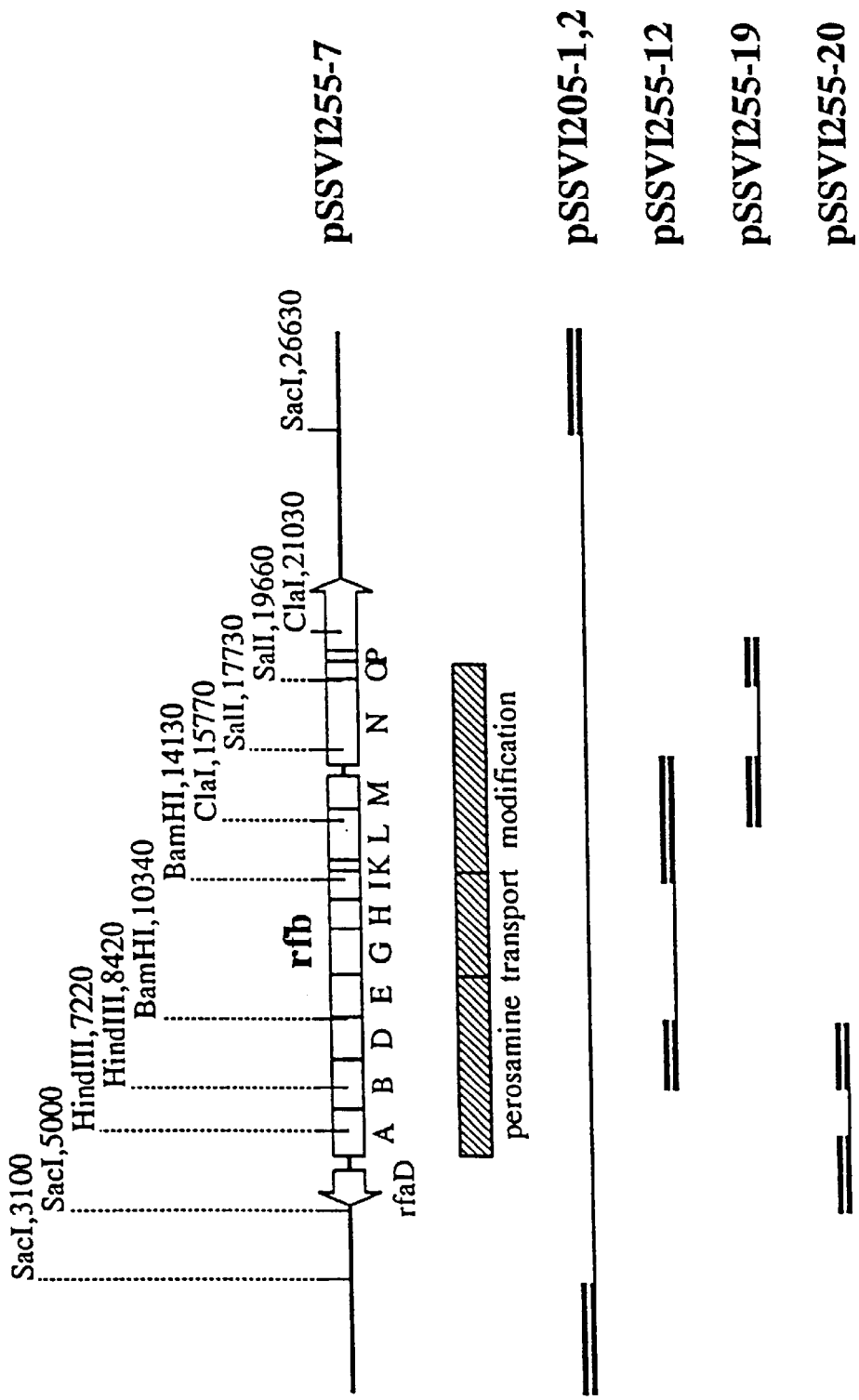

LIVE VACCINES AGAINST GRAM-NEGATIVE PATHOGENS, EXPRESSING HETEROLOGOUS O-ANTIGENS

This application is the national phase under 35 U.S.C. §371 of prior PCT International Application No. PCT/EP96/04334, which has an International filing date of Oct. 4, 1996, which designated the United States of America, the entire contents of which are hereby incorporated by reference.

The present invention relates to live attenuated gram-negative vaccine carrier strains which are useful for expression and delivery of heterologous O-antigens (O-PS) from gram-negative pathogens. Said strains are deficient in the expression of homologous O-PS due to a defined genetic modification, preferably a deletion, and, thus, capable of efficiently expressing a desired heterologous O-PS in such a way that it is covalently coupled either to homologous or heterologous LPS core lipid A. The present invention furthermore relates to live vaccine carrier strains containing a heterologous gene or a set of heterologous genes encoding O-PS. Preferably, said strains additionally contain genes necessary for the synthesis of complete smooth heterologous LPS. The present invention also relates to live vaccines comprising said strains, preferably for immunization against gram-negative enteric pathogens.

BACKGROUND OF THE INVENTION

Gram-negative enteric pathogens are the cause of a variety of diseases presenting with a broad spectrum of symptoms ranging from mild watery diarrhea to severe life-threatening symptoms such as fever, bloody diarrhea, perforation or ulceration of the stomach or intestine, alone or in combination. Examples of such diseases include typhoid fever, shigellosis, cholera, infections with enterotoxinogenic, enteropathogenic, and enterohemorragic *Escherichia coli*, and infections with *Heliobacter pylori* and *Campylobacter jejuni*.

The first stage of the infectious process occurs at the mucosal surface within the digestive tract. Thus, interfering with this initial stage of infection prior to the onset of symptoms offers a particularly attractive approach. The most effective means by which to accomplish this would be to evoke a local protective immune response through the use of an orally administered vaccine (Mestecky, J. Clin. Immunol. 7 (1987), 265–276; McGhee and Kiyono, Infect. Agents Dis. 2 (1993), 55–73; Walker, Vaccine 12 (1994), 387–400). At present, 2 live oral attenuated vaccines against enteric disease have been licensed for human use these being the Ty21a strain of *Salmonella typhi* for the prevention of typhoid fever and the CVD103-HgR strain of *Vibrio cholerae* for the prevention of cholera (Germanier and Furer, J.Infect.Dis, 131 (1975), 553–558; Levine et al., Lancet ii (1998), 467–470).

There exists a large body of evidence indicating that protection against several enteric pathogens, such as *S. typhi*, *E. coli*, and Shigella species is associated with the induction of an immune response against cell surface components, specifically the O-antigen moiety of LPS, commonly referred to as O-polysaccharide (O-PS). For example, immunity to shigellosis, subsequent to recovery from either naturally-acquired or experimentally-induced disease is correlated with a substantial rise in serum serotype-specific anti-LPS antibodies (DuPont et al., J.Infect.Dis. 125 (1972), 5–11; DuPont et al., J.Infect.Dis. 12 (1972), 12–16; Herrington et al., Vaccine 8 (1990), 353–357). Furthermore, epidemiological studies have also found that protection against Shigella infections in the field was associated with increased levels of serum anti-LPS antibodies (Cohen et al. , J.Infect.Dis. 157 (1988), 1068–1071). High levels of serum antibodies against Shigella LPS can be detected among individuals residing in areas where such species of Shigella are endemic, presumably acquired by natural exposure and/or infection with these pathogens.

LPS is an essential constituent of the gram-negative outer membrane and may account for up to 70% of the cell surface components. LPS is composed of 3 regions: the innermost being lipid A which is embedded into the phospholipid outer membrane bilayer. The core polysaccharide is attached to the lipid A moiety usually via 2-keto,3-deoxyoctonate (KDO). The core is usually comprised of 5 to 7 sugars. To date, 7 types of core molecules have been identified within the Enterobacteriaceae family and have been named Ra, R1, R2, R3, R4, K-12, and B. Compared with the Enterobacteriaceae, *V. cholerae* possess an unusual core structure in that it contains fructose and a single KDO molecule in the inner core (Kondo et al., Carbohydrate Res. 231 (1992), 55–64). The biosynthesis of the LPS core is encoded by the rfa locus. Among the Enterobacteriaceae, the rfa and rfb loci appear to be unlinked. In contrast, some evidence exists to suggest a close linkage of at least part of these two loci for *V. cholerae* (Manning et al., p. 77–94. In *Vibrio cholerae* and *Cholera*: molecular to global perspectives (1994). Wachsmuth K., Blake, P. A., and Olsvik Y. (eds.). Washington, D.C.: American Society for Microbiology).

The outermost portion of the LPS molecule is composed of the O-PS which consists of repeating saccharide units of variable length (Luderitz et al., Curr. Top. Membr. Trans. 17 (1982), 79–151; Raetz, Annu. Rev. Biochem. 59 (1990) 129–170). The O-PS region of the LPS molecule confers serospecificity to the bacteria. The LPS molecule interacts closely with other molecules expressed on the outer membrane surface such as porins and other outer membrane proteins (OMP), which determine the permeability of the outer membrane. It is known that the assembly of OMP as well as secretion of proteins from the cell is affected by mutations in the LPS of *E. coli* (Laird et al., J. Bacteriol. 176 (1994), 2259–2204; Stanley et al., Mol. Microbiol. 10 (1993) 781–787).

Serospecificity is conferred not only by the sugars present in the O-PS but also by their chemical linkage and sequence (Lüderitz et al., Curr. Top. Membr. Trans. 17 (1982), 79–151). Therefore, the O-PS is highly variable between gram-negative bacterial species whereas the core polysaccharide is relatively constant within a given species or genera (Lüderitz et al., Curr. Topics in Membranes and Transport 17 (1982), 79–151; Jansson et al., Eur.J.Biochem. 115 (1981), 571–577). For example, the genus Shigella includes a total of 47 known serotypes divided among the 4 predominant pathogenic species which are *S. dysenteriae* (subgroup A, 12 serotypes), *S. flexneri* (subgroup B, 13 serotypes) *S. boydii* (serogroup C, 18 serotypes) and *S. sonnei* (subgroup D; 1 serotype) (Ewing, In: Ewing W H, ed. Edwards and Ewing's identification of Enterobacteriaceae fourth edition. New York: Elsevier Sci. Publish. Comp. (1986), 135–172). For example, in *S. sonnei*, the O-PS consists of a repeated disaccharide unit with 2 unusual sugars, 2-amino-2-deoxy-L-alturonic acid linked to 2-acetamido-4-amino-2,4,6-trideoxy-D-galactose by a 1,4 linkage (Kenne et al., Carbohydrate Res. 78 (1980), 119–126). In contrast, the O-PS of serotype 1 of *S. dysen-* teriae (which is the most common cause of dysentery) is composed of repeating blocks of rhamnose-rhamnose-galactose-N-acetylglucosamine (Ewing and Lindberg, In: Bergan T. (ed) Methods in microbiology vol.14., Academic Press, London, pp. 113–142). The O-PS of *V. cholerae* 01 is comprised of 17–18 perosamine subunits each of which is acylated with 3-deoxy-L-glycero-tetronic acid. Quinovosamine has also been found in low concentrations but its location within the O-PS of *V. cholerae* 01 is unknown (Redmond, FEBS Lett. 50 (1975), 147–149; Kenne et al., Carbohydrate Res. 100 (1982), 341–349).

The enzymes involved in the biosynthesis of enterobacterial O-PS are coded for by the rfb locus. In the case of Shigella species, an additional gene, termed rfc, encodes the O-PS polymerase which functions to polymerize the individual repeat units into chains of varying length. In most Shigella species, the rfb/rfc loci are located on the chromosome (Klena and Schnaitman, Microbiol. Rev. 57 (1993), 655–682). However, in some species of Shigella, all or part of the rfb locus is located on a plasmid episome (Maurelli and Sansonetti, Ann. Rev. Microbiol. 42 (1988), 127–150). An additional gene, termed rfe, which is involved in the synthesis of the enterobacterial common antigen (ECA) is also required for O-PS synthesis in Salmonella species of the O-antigen groups C1 and L (Kuhn et al., FEMS Microbiol. Rev. 54 (1988), 195–222; Mäkelä et al., J. Gen. Microbiol. 60 (1970), 91–106), as well as in some serotypes of *E. coli* and in *S. dysenteriae* type 1 (Kuhn et al., FEMS Microbiol. Rev. 54 (1988), 195–222; Schmidt et al., J. Bacteriol. 127 (1976), 755–762; Klena and Schnaitman, Microbiol. Rev. 57 (1993), 655–682). A further gene, termed rfp, encodes a galactosyl transferase and is necessary for the production of full-length O-PS in *S. dysenteriae* type 1 (Klena and Schnaitman, Microbiol. Rev. 57 (1993), 655–682). In addition, serotype conversion can be accomplished via substitution of an O-PS sugar promoted by certain phages lysogenic for Salmonella species and *S. flexneri* (Clark et al., Gene 107 (1991), 43–52; Verma et al. Gene 129 (1993) 101).

In the specific case of *V. cholerae*, the entire rfb locus is chromosomally encoded. Genes involved in perosamine synthesis (rfbABDE), transport of the polymerized O-PS to the cell surface (rfbGHI), and in the transfer of tetronic acid onto the perosamine subunit (rfbKLMNO), are sequentially organized to constitute a single operon. In addition, four genes of unknown function, termed rfbPQRS, constitute the 3' end of the operon. Directly adjacent to the rfb operon is the rfbT gene which determines the Inaba and Ogawa serospecificity of 01 strains of *V. cholerae*. It was recently determined that the Inaba serotype strains, are rfbT mutants (Manning et al., p.77–94. In *Vibrio cholerae* and Cholera: molecular to global perspectives (1994). Wachsmuth, K., Blake, P. A., and Olsvik, φ. (eds.). Washington, D.C.:American Society for Microbiology.

As noted above, the induction of a local intestinal immune response may be the most efficient means by which to prevent infection with a number of enteric pathogens. A proven and effective method by which to accomplish this is through the use of live oral attenuated vaccine strains. Vaccine strains such as *S. typhi* Ty21a and *V. cholerae* CVD103-HgR noted above undergo an abortive infectious process thereby inducing an immune response closely resembling that effected by natural infection. The above two strains possess the distinct advantage of being extremely safe in humans (Levine et al., Rev. Infect. Dis. 11 (1989), (Suppl 3), 552–567; Cryz et al., Infect. Immun. 61 (1993), 1149–1151; Levine and Kaper, Vaccine 11 (1993), 207–212).

Safety has been found to be the most difficult attribute to achieve in the development of live oral vaccine strains. Most often, candidate vaccine strains either induce a protective immune response but with an unacceptable rate of adverse reactions or are safe but non-protective (Lindberg, In Vaccine and Immunotherapy. Cryz Jr,S. J. (ed.). New York: Pergamon Press Inc. (1991), pp. 95–112; Levine and Hone, In Vaccine and Immunotherapy. Cryz Jr,S. J. (ed.). New York: Pergamon Press Inc. (1991), pp. 59–72).

Given the above, it is desirable to utilize approved live oral attenuated vaccine strains as carriers for the delivery of heterologous vaccine antigens to the intestinal tract. Attempts to utilize the *S. typhi* Ty21a strain as a carrier for vaccine antigens has not yielded promising results (Curtiss III, In: New generation vaccines. Woodrow, G. C. and Levine, M. M. (eds.) New York: Marcel Dekker Inc. (1990), pp. 161–188; Cardenas and Clements, Clin. Microbiol. Rev. 5 (1992), 328–342). This in large part can be accounted for by the fact that this strain was developed using a potent chemical mutagen which induced multiple mutations. Therefore, the precise attenuating mutation is unknown. Furthermore, the Ty21a strain replicates poorly in vivo requiring multiple doses of vaccine to be administered. In contrast, the CVD103-HgR vaccine strain was constructed using recombinant DNA technology allowing for the precise genetic lesions to be identified (Ketley et al., FEMS Microbiol. Lett. 111 (1993), 15–22). Furthermore, this strain appears to replicate well in vivo as evidenced by the fact that only a single dose of vaccine is required to induce a high level of immunity against experimental cholera (Levine et al., Lancet ii (1988), 467–470).

Initial attempts to utilize the above strains as carriers envisioned the development of bivalent vaccines. In such a case, the recombinant strain would co-express two O-PS antigens. However, the successful development of such bivalent vaccine strains has proven to be extremely difficult for a variety of reasons, some of which are just becoming apparent. First, experimental data has shown that covalent linkage between the O-PS moiety and LPS core region appears to be a prerequisite for the efficient induction of immunity (Beckmann et al., Nature 201 (1964), 1298–1301; Kuhn et al., FEMS Microbiol. Rev. 54 (1988), 195–222; Attridge et al., Microb. Path. 8 (1990), 177–188; Baron et al., Infect. Immun. 55 (1987), 2797–2801). Second, the co-expression of two O-PS entities often results in the masking of one antigen thereby blunting the immune response (Attridge et al., Microb. Path. 8 (1990), 177–188; Forrest et al., Vaccine 9 (1991), 515–520). Third, the recombinant strain must still fully express the protective antigens associated with the carrier strain. Finally, expression of the foreign antigen should not adversely affect the ability of the bivalent strain to either replicate in vivo or colonize the mucosal surfaces.

The following examples illustrate the practical problems encountered in the construction of bivalent vaccine strains. Formal et al. (Infect. Immun. 34 (1981), 746–750) have introduced the 120 Mdal virulence plasmid of *S. sonnei* into *S. typhi* Ty21a via conjugation. The resulting hybrid strain, termed 5076-1C, expressed the O-PS antigen of *S. sonnei* encoded by the plasmid on the surface of Ty21a as a capsular-like material unbound to *S. typhi* LPS core (Seid et al., J. Biol. Chem. 259 (1984), 9028–9034). Immunization of volunteers with this strain resulted in a vigorous anti-*S. sonnei* LPS antibody response. However, in challenge studies, various lots of this vaccine were unable to consistently afford significant protection against *S. sonnei* disease (Herrington et al., Vaccine 8 (1990), 353–357; Black et al., J. Infect. Dis. 155 (1987), 1260–1265; Van De Verg et al., Infect. Immun. 58 (1990), 2002–2004). The precise reason for this variable protection has not been identified. Possible explanations include, 1) the presence of the *S. sonnei* antigen on the surface of the Ty21a strain interfered with its ability to effectively colonize, 2) the virulence plasmid was shown to be genetically unstable within Ty21a giving rise to spontaneous deletions which interfered with the expression of the *S. sonnei* O-PS and other virulence-associated antigens, 3) expression of the *S. sonnei* plasmid in Ty21a could have led to a deleterious effect manifested only in vivo such as reduced survival, multiplication or colonization.

A bivalent vaccine strain was constructed by introducing the genes encoding for *V. cholerae* O-PS biosynthesis into Ty21a yielding strain EX645. This strain induced a modest anti-*V. cholerae* LPS immune response when fed to volunteers even though the heterologous O-PS was coupled to the LPS core (Forrest et al., J. Infect. Dis. 159 (1989), 145–146). Only a modest level of protection was afforded against experimental cholera following immunization with EX645. Subsequent studies showed that the longer *S. typhi* O-PS probably masked the somewhat shorter *V. cholerae* O-PS units accounting for the poor immune response. A derivative of EX645, termed EX880, was developed by inactivating genes involved in the expression of the *S. typhi* O-PS. EX880 was found to induce a far more vigorous anti-*V. cholerae* LPS antibody response compared to EX645 (Attridge et al., Infect. Immun. 59 (1991), 2279–2284). The anti-*S. typhi* LPS response was minimal.

The rfb/rfc and the rfa$_{R1}$ loci of *S. sonnei* were introduced into CVD103-HgR by the use of compatible plasmids (Viret et al., Mol. Microbiol. 7 (1993), 239–252). This allowed for the efficient expression of the *S. sonnei* O-PS coupled to LPS core. However, when these same genetic loci were introduced into the chromosome of CVD103-HgR (strains CH3 and CH9), little if any *S. sonnei* O-PS was covalently coupled to LPS core (Viret and Favre, Biologicals 22 (1994), 361–372). Instead, the material was expressed on the surface of CVD103-HgR as a capsular-like material.

The above observations suggest the following, 1) heterologous O-PS can be efficiently coupled to homologous or heterologous LPS core only if the synthesis of homologous O-PS is suppressed, 2) under appropriate conditions it may be possible to covalently couple heterologous O-PS to the unique core of *V. cholerae* thereby obviating the need for introducing genes coding for a heterologous core molecule, and 3) the co-expression of two distinct O-PS molecules by the same carrier strain resulting in a bivalent vaccine may not be feasible. Thus, the efficient simultaneous expression of two complete LPS molecules each presenting different O-PS moieties may be beyond the capacity of a single host strain. Possible reasons include interference with the expression of the respective genes at the transcriptional level, competition for limiting components involved in the biosynthesis of the outer membrane structure, such as molecules involved in the transposition of the O-PS molecule to the outer surface of the cell, or competition between the O-PS molecules for transfer or binding to available sites on the LPS core molecule.

In an attempt to circumvent these problems previously spontaneous, undefined mutants of *V. cholerae* CVD103-HgR which are deficient in the synthesis of O-PS were isolated. Such strains were capable of supporting the covalent attachment of *S. sonnei* O-PS encoded by the chromosomally integrated rfb/rfc loci to an LPS core. However, the undefined nature of the mutation(s), present in such strains render them unacceptable for human use.

SUMMARY OF THE INVENTION

Thus, the technical problem underlying the present invention is to provide live attenuated vaccine carrier strains, which are useful for the expression and delivery of heterologous O-antigen (O-PS) from gram-negative bacteria in such a way that the heterologous O-PS can induce an immune response and which are safe and acceptable for administration as a vaccine.

The solution to said technical problem is achieved by providing the embodiments characterized in the claims. It has been surprisingly found that a defined genetic modification can be introduced in a live attenuated vaccine strain, which does not interfere with the functions of the carrier strain required in order to make said strain suitable as carrier for a heterologous antigen, and which leads to a deficiency of said strain in the synthesis of homologous O-PS, thereby allowing to efficiently express a desired heterologous O-PS in such a manner that the heterologous O-PS is covalently coupled to the LPS core and can induce an immune response.

The embodiments of the present invention inter alia allow for the construction of monovalent vaccine strains with the following characteristics, 1) use of a live oral attenuated vaccine strain, preferably *V. cholerae* CVD103-HgR, suitable for human use as a carrier for heterologous antigens, 2) modification of said carrier strain so as to render it deficient in the synthesis of homologous O-PS by introduction of precise mutations, e.g. within the rfb gene which are non-lethal, halt the synthesis of homologous Inaba O-PS and allow for the expression and covalent coupling of heterologous O-PS to the LPS core, 3) containing genes necessary for the production of heterologous, polymerized LPS molecules derived from other enteric pathogens and expressing them, wherein stable expression is achieved by integration of the cloned heterologous genes at a site which does not adversely affect the phenotype of the carrier strain, specifically, those traits which would allow it to induce a protective immune response following oral administration, 4) expression of the heterologous O-PS genes in such a manner that the encoded O-PS is covalently coupled to either the LPS core of the carrier strain or a heterologous LPS core produced by the carrier strain following the introduction of the appropriate rfa locus, 5) the LPS molecule bearing the heterologous O-PS moiety is expressed on the surface of the carrier strain, preferably integrated into the outer membrane protein, and 6) the genotype/phenotype of the carrier strain which renders it suitable for human use is maintained.

In order to develop such vaccine strains various genetic modifications were introduced in the genes for expression of the O-PS of the carrier strain in order to eliminate synthesis of the O-PS.

Surprisingly, the deletion of the entire Inaba rfb locus (about 20 kb) had a lethal effect upon CVD103-HgR and its *S. sonnei* rfb/rfc-bearing derivatives (strains CH3 and CH9). Therefore, it was assumed that there must be genes encoding for essential functions within or adjacent to the rfb locus and that strains deficient in such functions would be unable to multiply, presumably due to their inability to synthesize a functioning outer membrane structure. It was therefore sought to introduce specific deletions, for example, within three distinct regions of the rfb locus. The goal was to try to introduce non-lethal deletions into the rfb locus which would, in addition to halting expression of the homologous Inaba O-PS moiety, support the covalent coupling of the heterologous *S. sonnei* O-PS to the Inaba LPS core. The first such construct was a rfbEGHI mutant. The rfbE locus encodes the perosamine synthetase whereas the rfbG, H, and I loci are involved in the transport of the Inaba O-PS through the outer membrane (Manning et al. p.77–94. In *Vibrio cholerae* and Cholera: molecular to global perspectives (1994). Wachsmuth K., Blake, P. A., and Olsvik φ. (eds.). Washington, D.C.:American Society for Microbiology). The rfbEGHI deletion was found to be lethal in CVD103-HgR. In a second strain, deletion of the rfbN locus (which is involved in the synthesis of the perosamine substituent 3-deoxy-L-glycero-tetronic acid), unexpectedly resulted in only weak production of the heterologous *S. sonnei* O-PS which was unbound to the Inaba core. Therefore specific gene functions within the Inaba rfb locus are useful for both the expression of the heterologous *S. sonnei* rfb genes and its covalent coupling to the *V. cholerae* LPS core in as of yet unidentified manner. Next the rfbA and rfbB loci were inactivated by deleting a 1.2 kb fragment overlapping the junction between the two loci. These loci are involved in the synthesis of the perosamine component of the Inaba O-PS. Specifically, the RfbA protein is associated with enzymes having phospho-mannose isomerase or mannose-1-phosphate guanyl transferase activity while the rfbB loci encodes a putative phospho-manno mutase. The introduction of the rfbA/rfbB mutation into CVD103-HgR containing the *S. sonnei* rfb/rfc loci allowed for the expression and covalent coupling of the *S. sonnei* O-PS to the Inaba LPS core giving rise to full length hybrid LPS molecules. Recombinant strains expressing the Inaba rfbA/rfbB deletion together with the *S. sonnei* rfb/rfc loci with or without the R1 core were found to be genotypically and phenotypically stable upon passage in vitro. Furthermore, these strains possessed all the characteristics of the CVD103-HgR strain which render it suitable for human use, including, 1) lack of cholera toxin activity, 2) production of non-toxic B subunit of *cholera* toxin, 3) expression of toxin co-regulated pili, and 4) the ability to grow in the presence of elevated levels of Mercury ions.

Accordingly, the present invention relates to live attenuated vaccine strain against gram-negative enteric pathogens characterized by the following properties:

(a) deficiency to express homologous O-PS due to a, defined genetic modification, and (b) capability to efficiently express heterologous O-PS in such a manner that said heterologous O-PS is covalently coupled to the LPS core.

As used herein, the term "defined genetic modification" encompasses any modification(s) which has (have) been introduced by recombinant DNA techniques and which is (are), in contrast to modifications introduced by random mutagenesis or due to spontaneous mutations, defined with respect to its nature and location. Said modifications can be deletions, additions, substitutions or rearrangements of nucleotides, but should preferably not give raise to the occurrence of revertants. Suitable genetic modifications in accordance with the present invention can be introduced by the person skilled in the art following the teaching given in the Examples below. Such modifications should not interfere with the functions of the carrier strain required in order to make said strain suitable as carrier for a heterologous O-PS, but should sufficiently eliminate the expression of homologous O-PS. For example, said modifications affecting the biosynthesis of the homologous O-PS should not adversely affect the expression of genes which are essential for the synthesis of complete LPS comprised of heterologous O-PS, e.g. the genes involved in the synthesis of lipid A, the LPS core, the synthesis and transport of O-PS to the outer cell surface and anchoring the LPS molecules into the outer membrane.

Due to said modifications said strains synthesize LPS molecules which only consist of the homologous lipid A and homologous and/or, in a specific embodiment which is described below, a heterologous LSP core. Preferably, said modifications are deletions. As used herein, the term "deficiency to express homologous O-PS" means that the expression of the homologous O-PS is entirely eliminated or at least reduced such that the efficient expression of the desired heterologous O-PS, and its covalent binding to the LPS core of the carrier strain or, alternatively, to a heterologous LPS core is made possible.

As used herein, the term "capability to efficiently express heterologous O-PS" means the capability to express said O-PS in such a way, that the amounts of heterologous O-PS produced are sufficient to elicit an immune response.

In a preferred embodiment, the vaccine strain carries a defined genetic modification within the genes involved in O-PS biosynthesis contained in the rfb, rfc, and/or rfp loci or any combination thereof.

In a particularly preferred embodiment, the vaccine strain carries a defined genetic modification within the rfbA-, rfbB-, rfbD and/or rfbE-gene or any combination thereof, preferably within the rfbA- and/or rfbB-gene.

Most preferred is a vaccine strain, wherein said genetic modification is a deletion corresponding to the deletion shown for pSSVI255-20 (DSM depository number DSM13426) in FIG. 1. This deletion is located at the beginning of the rfb$_{inaba}$ operon and concerns the elimination of a 1.2 kbp HindIII fragment. It inactivates the rfbA- and rfbB-genes which are involved in the biosynthesis of the perosamine O-antigen subunit.

Suitable vaccine strains can be selected by the person skilled in the art, depending on the desired purpose. Such strains are, for example, CH19 (DSM depository number DSM13420), CH21 (DSM depository number DSM13421), CH22 (DSM depository number DSM13422), CH24 (DSM depository number DSM13423), CH25 (DSM depository number DSM13424) or CH30 (DSM depository number DSM13425), described below.

In a preferred embodiment, said vaccine strain is an *E. coli* strain, a strain of the genus Shigella, *S. typhi*, O1 or O139 *V. cholerae, Heliobacter pylori* or *Campylobacter jejuni*. Preferred *S. typhi* strains are *S. typhi* Ty21a, *S. typhi* CVD908, or *S. typhi* CVD908 containing additional attenuating mutations. Examples of additional attenuating mutations are mutations in the viaB or htpR genes encoding transcriptional signals such as the RpoS sigma factor or in genes involved in virulence traits such as the resistance to environmental stress or the capacity to adapt to new growth conditions or in genes involved in the synthesis of aromatic acids.

Preferred *V. cholerae* strains are *V. cholerae* CVD103-HgR, *V. cholerae* CVD103-HgR, CVD110, CVD111, CVD112, Bengal-15 or Peru-14.

Preferred Shigella strains are *S. dysenteriae, S. sonnei, S. boydii*, or *S. flexneri* serotype Y.

The above vaccine strains can be used for the efficient expression of heterologous O-PS. For this purpose a heterologous gene or a set of heterologous genes coding for O-PS are inserted into the vaccine strain by methods known to the person skilled in the art, for example by methods described in the Examples, below.

Accordingly, the present invention relates to vaccine strains further characterized by the presence of a heterologous gene or a set of heterologous genes coding for O-PS.

The insertion of said gene(s) encoding a heterologous O-PS should be carried out in such a manner that (i) said gene(s) are stably expressed and allow for the synthesis of complete full-length, smooth LPS essentially indistinguishable from the parent strain, and (ii) an intact hybrid LSP is formed composed of the lipid A of the vaccine strain coupled to the homologous core region. Thus, when inserting said gene(s) the person skilled in the art should i) use a bacterial carrier strain devoid of the genes coding for the homologous O-PS, ii) use a plasmid, for example pMAK700oriT, composed of all the genes coding for the heterologous O-PS, flanked by homologous genetic regions corresponding to the locus where the said heterologous O-PS genes are to be inserted, and iii) then proceed as described in Example 3, below.

In a preferred embodiment of the vaccine strains, the heterologous gene(s) is (are) present either on a plasmid vector or stably integrated into the chromosome of said strain at a defined integration site which is to be non-essential for inducing a protective immune response by the carrier strain.

The set of heterologous genes should be cloned in a deletion vector composed of a thermosensitive replicon, for example, pMAK700oriT and a homologous genetic region corresponding to the gene where the insertion is to take place. The heterologous genes will be cloned in the middle of the homologous region. For the integration of the heterologous genes this plasmid should be introduced into a suitable carrier strain and thereafter handled like in Examples 5, 6, 7 and 8, below.

Suitable sites for integration of the heterologous gene(s) into the chromosome of the vaccine strain are genes which in no way will effect properties of the strain necessary for its immunogenecity and safety.

In a preferred embodiment, said heterologous gene or set of heterologous genes are integrated into either the hlyA, hlyB, rfbA, and/or rfbA/rfbB loci of V. cholerae.

A further particular preferred embodiment relates to a S. typhi strain, wherein said heterologous gene or set of heterologous genes are integrated into either the $H_2S$ production gene, ilv, viab, htpR genes encoding transcriptional signals such as the RpoS sigma factor, genes involved in virulence traits such as the resistance to environmental stress or the capacity to adapt to new growth conditions, or any gene involved in the synthesis of aromatic acids. Genes involved in the resistance to environmental stress or the capacity to adapt to new growth conditions are genes of the OmpR-EnrZ system, PhoP-PhoQ system and cya-crp transcription regulation system. Genes involved in the synthesis of aromatic acids are, for example, aroA, aroC and aroD.

Alternatively, the above vaccine strains contain the rfa, rfe, rfp, and/or any additional gene(s) necessary for the synthesis of complete smooth heterologous LPS which are integrated in tandem into a single chromosomal site or independently integrated into individual sites.

Additional genes necessary for the synthesis of complete smooth heterologous LPS are for example, rfc and rff. Integration of the above genes in such a way that they are correctly and in a coordinate manner expressed can be carried out by the person skilled in the art according to well known methods or, for example, described in Hamilton et al., J. Bacteriology 171 (1989), 4617–4622.

Such vaccine strains allow expression of heterologous O-PS which is covalently coupled to a heterologous LPS core region, which, preferably, exhibits a degree of polymerization essentially indistinguishable from that of native LPS produced by the enteric pathogen. Such vaccine strains can, if desired, modified in such a way that they are deficient in the synthesis of homologous LPS core.

In a preferred embodiment, the heterologous rfa genes encode the Ra, R1, R2, R3, R4, K-12 or B LPS core, preferably the R1 core.

The invention also relates to a live vaccine comprising the above vaccine strain and optionally a pharmaceutically acceptable carrier and/or a buffer for neutralizing gastric acidity and/or a system for delivering said vaccine in a viable state to the intestinal tract.

Said vaccine comprises an immunoprotective and non-toxic amount of said vaccine strain. Suitable amounts can be determined by the person skilled in the art and are typically $10^7$ to $10^9$ bacteria.

Pharmaceutically acceptable carriers, suitable neutralizing buffers, and suitable delivering systems can be selected by the person skilled in the art.

In a preferred embodiment said live vaccine is used for immunization against gram-negative enteric pathogens.

The mode of administration of the vaccines of the present invention may be any suitable route which delivers an immunoprotective amount of the vaccine to the subject. However, the vaccine is preferably administered orally or intranasally.

The invention also relates to the use of the above vaccine strains for the preparation of a live vaccine for immunization against gram-negative enteric pathogens. For such use the vaccine strains are combined with the carriers, buffers and/or delivery systems described above.

The following examples illustrate the invention.

In summary, the utility of Inaba rfbA/rfbB deletion mutants as carriers or vectors for heterologous O-PS antigens is illustrated. The rfb locus of O139 V. cholerae was cloned on a about 32 kb fragment and integrated into the hlyA::mer locus of the rfbA/rfbB deletion mutant. This construct expressed O139 O-PS which was coupled to the Inaba core and recognized by specific anti-O139 antibodies. Similarly, the rfb/rfp loci from S. dysenteriae which allow the production of O-PS were cloned on a 13.8 kb fragment and integrated into the rfbA/rfbB deletion mutant of CVD103-HgR as described above. In this construct the S. dysenteriae O-PS was produced on the cell surface, covalently coupled to the core and recognized by specific anti-S. dysenteriae O-PS. However, this construct expressed only very short LPS molecules instead of the full ladder-like structure associated with native S. dysenteriae LPS. However, the addition of the rfe gene from E. coli, believed to be involved in the polymerization of O-PS, on a plasmid or integrated into the chromosome of the construct, resulted in the synthesis of a LPS with a phenotype indistinguishable from that of native S. dysenteriae.

EXAMPLE 1

Cloning and Physical Mapping of the rfb Locus From V. cholerae CVD103-HgR

Preparation of the gene bank. A V. cholerae CVD103-HgR DNA gene bank was prepared in the low-copy number cosmid pLAFR5 (Keen et al., Gene 70 (1988), 191–197). DNA fragments from isolated CVD103-HgR chromosomal DNA were generated by partial Sau3A restriction and size fractionated on a sucrose gradient. Fractions containing 20 to 30 kb fragments were purified and ligated to the BamHI and ScaI-cut vector. The ligated mixture was packaged in vitro (Gigapack II Plus packaging kit, Stratagene GMBH, Zürich, Switzerland) according to the manufacturer's instructions. The packaged DNA was then transfected into E. coli strain HB101 and the resulting culture was plated out onto LB plates containing 12.5 µg/ml tetracycline (LBTc plates)

to select for transfectants. Resistant colonies were pooled, aliquoted and the aliquots were stored in 40% glycerol at −70° C.

Screening of the gene bank. One frozen aliquot of the cosmid bank was diluted and plated out on LBTc plates. Arising colonies were transferred onto nitrocellulose filters. Filters were then processed for immunodetection according to published protocols (Sambrook et al., Molecular cloning, 2nd edition, Cold Spring Harbor Laboratory Press, Cold Spring Harbor USA, (1989)). Probing the filters with the Inaba/Ogawa specific monoclonal antibody (mAb) VCO4 (previously called H4; Gustafsson and Holme, J. Clin. Microbiol. 18 (1983), 480–485) allowed the isolation of several independent clones, which remained strongly positive when retested with the same mAb. Three clones named pSSVI255-3, pSSVI255-5, and pSSVI255-7 were further characterized.

Restriction analysis of pSSVI255-3, pSSVI255-5 and pSSVI255-7. The restriction pattern obtained with a variety of restriction enzymes indicated a large degree of overlap among the three clones. All three clones were mapped using EcoRI, SacI, and PstI. With the aid of a known DNA sequence of an approximately 20 kb SacI fragment encompassing the rfb locus from the El Tor Ogawa *V. cholerae* strain O17 (Manning et al., p.77–94. In *Vibrio cholerae* and *Cholera*: molecular to global perspectives (1994). Wachsmuth K., Blake, P. A., and Olsvik Y. (eds.). Washington, D.C.:American Society for Microbiology, the exact location of the rfb locus in each clone could be determined. On the basis of this information, clone pSSVI255-7 (FIG. 1) was exclusively used for further work.

EXAMPLE 2

Construction of Deletion Plasmids for the Introduction of Chromosomal Deletions in *V. cholerae*

In order to maximize the probability of obtaining a successful deletion within the rfb locus of *V. cholera*, four distinct fragments within the rfb locus were selected to be individually deleted. FIG. 1 summarizes the various deletion vectors that were generated. Plasmids pSSVI205-1 and pSSVI205-2 were constructed by removing 23.5 kb of DNA between the outer SacI sites in pSSVI255-7, and subcloning, in both orientations, the remaining insert into the blunted HindIII site of prvAK700oriT (FIG. 2). The latter plasmid corresponds to the suicide vector pMAK700 (Hamilton et al., J. Bacteriol. 171 (1989), 4617–4622) made mobilizable by the addition of the oriT region from plasmid pJFF350 (Fellay et al., Gene 76 (1989), 215–226). Plasmid pSSVI255-12 corresponds to pMAK700oriT bearing the 10.5 kb SalI-HindIII central fragment of pSSVI255-7 from which the 3.8 kb internal BamHI fragment was deleted. This deletion inactivates the rfbEGHI genes. Gene rfbE is the putative perosamine synthetase, whereas rfbG, H and I are involved in the transport of the $rfb_{inaba}$-encoded O-PS components through the outer membrane (Manning et al., p.77–94. In *Vibrio cholerae* and *Cholera*: molecular to global perspectives (1994). Wachsmuth K., Blake, P. A., and Olsvik ϕ. (eds.). Washington, D.C.:American Society for Microbiology. Plasmids pSSVI255-19 and pSSVI255-20 were both derived from pSSVI25S-7 through subcloning of defined restriction fragments into the high-copy-number vector pMTL22p (Chambers et al., Gene, 1988, 68:139–149), deletion of a central region, and further. subcloning of the resulting insert into pMAK700oriT. pSSVI255-19 corresponds to the 5.3 kb ClaI fragment (Map position 15770 to 21030, FIG. 1) from which the internal 1.9 kb SalI fragment was deleted. The deletion overlaps the, rfbN gene which is believed to be involved in the synthesis of the perosamine substituent 3-deoxy-L-glycero-tetronic acid. pSSVI255-20 corresponds to the 5.3 kb BamHI-SacI fragment located at the beginning of the $rfb_{Inaba}$ operon (Map position 18500 to 23400), from which the 1.2 kb HindIII internal fragment was deleted. This deletion inactivates the rfbA and rfbB genes which are directly involved in biosynthesis of the perosamine O-antigen subunit. RfbA function is closely associated to proteins with phosphomannose isomerase or mannose-1-phosphate guanyl transferase activity and RfbB is a putative phospho-manno mutase.

EXAMPLE 3

Introduction of rfbAB Deletions in Target Carrier Strains: Construction of Strains CH15, CH19 and CH30

The various plasmids described in Example 2 were first transferred by electroporation into the *E. coli* mobilization strain S17.1 (Simon et al. Bio/Technology 1 (1983), 784–791) and then mobilized into *V. cholerae* CVD103-HgR. In addition, pSSVI255-20 was mobilized into the El Tor Ogawa vaccine strain CVD111.

Transconjugants were isolated by plating at 30° C. on selective BHI-Cm plates. The transconjugants were then propagated at 30° C. in liquid cultures (BHI-Cm medium) and suitable dilutions were plated on BHI-Cm plates and incubated at 30° C. or 41–42° C. Typically, the plating efficiency at 41–42° C. was about $10^4$-fold lower than at 30° C. Since, by virtue of its thermosensitive replicon, the plasmid is unable to replicate at 41° C. or more, colonies at the non-permissive temperature should arise from those rare cells carrying the entire deletion plasmid in, their chromosome. A series of colonies capable of growth at 41–42° C. were further streaked onto BHI-Cm plates incubated at 41–42° C. The selection of cells free of vector sequences was performed via streaking on non-selective BHI plates incubated at 30° C. Subsequently, immunological screening allowed for the isolation of colonies which responded negative for the VCO4 mAb. This antibody recognizes both the Ogawa and Inaba O-PS. These colonies were further screened to confirm that they had lost the chloramphenicol resistance trait inherent to the vector.

Such stable integrants were however not always isolated, indicating that some deletions were lethal. Thus, implementation of strains in which either the entire rfb locus or the rfbEGHI genes were deleted could not be obtained. The strain obtained by introduction of the rfbN deletion in CVD103-HgR using pSSVI255-19 was designated CH15, and rfbAB deletion mutants in CVD103-HgR and CVD111 using pSSVI255-20 were named CH19 and CH30, respectively. These deletion strains were genetically characterized by Southern hybridization using probes specific for the rfb locus. The genetic structure of all strains tested was found to be conform to expectations.

EXAMPLE 4

Introduction of rfbAB Deletions in Recombinant *V. cholerae* Strains Expressing *S. sonnei* O-PS Alone or in Combination With the *E. coli* rfaR1 LPS Core. Construction of Strains CH13, CH14, CH17, CH21

The above described plasmids were mobilized into strains CH3 and CH9 as described in Example 3.

As was the case for CVD103-HgR, introduction of the entire rfb locus deletion in CH3 or CH9 could not be achieved, presumably due to its lethal effect. Likewise, introduction of the 2 kb SalI deletion from pSSVI255-19 or the 1.2 kb HindIII deletion from pSSVI255-20 were not successful in strain CH3. The rfbEGHI deletion mutants arising from the integration of pSSVI255-12 into CH3 and CH9 are referred to as CH13 and CH14, respectively. Insertion of the rfbN deletion in CH9 using pSSVI255-19 was designated CH17, and a CH9 deletion mutant carrying the rfbAB deletion from pSSVI255-20 was named CH21. These deletion mutants were genetically characterized by Southern hybridization using probes specific for either the rfb$_{Inaba}$ or rfb/rfc$_{sonnei}$ loci in addition to a probe for the hlyA gene, the integration target for the rfb/rfc$_{sonnei}$ locus. The genotype of all strains tested was found to be conform to expectations.

EXAMPLE 5

Integration of the rfb/rfc$_{sonnei}$ Locus Into CH19. Construction of Strain CH22

Since we could not produce a CH3 deletion mutant using pSSVI255-20, a genotypically similar strain, CH22, was constructed by the reverse approach, namely the integration of rfb/rfc$_{sonnei}$ genes carried on plasmid pSSVI201-1 (FIG. 3) into the chromosome of CH19. pSSVI201-1 was initially used for the construction of strain CH9. The plasmid was mobilized from the *E. coli* strain S17.1 (pSSVI201-1) into CH19. A pool of transconjugants was then submitted to the integration procedure exactly as described in Example 2, except that the presence of the intact rfb/rfc$_{sonnei}$ locus was checked at each step of the procedure by immunological screening using mAB Sh5S (Viret et al., Infect. Immun. 60 (1992), 2741–2747). A stable Cm$^s$/Sh5S+ integrant was isolated and named CH22 (FIG. 4).

EXAMPLE 6

Integration of the rfb Locus From *V. cholerae* O139 Strain MO45 Into CH19: Construction of Strain CH25

Construction and screening of a DNA gene bank. A chromosomal gene bank derived from the wild type *V. cholerae* O139 strain MO45, the reference O139 epidemic strain, was constructed in pLAFR5 following the same procedure than that described in Example 1. The bank was then immunologically screened using an MO45-specific rabbit polyclonal antibody. A total of 13 cosmid clones were isolated which strongly reacted with the polyclonal antibody. These clones were then submitted to restriction analysis using a variety of restriction enzymes in order to determine the level of overlapping.

LPS expression in *E. coli*. LPS small-scale preparations (minipreps) were made from strains selected on the basis of the restriction pattern of the plasmids. Aliquots from these minipreps, together with LPS minipreps from the negative controls CH19 and HB101 (pSSVI212-15) and the positive control MO45, were then analyzed by silver stained SDS-PAGE and immunoblotting (Western blot) using as primary antibody the anti-O139 polyclonal serum described above. The developing antibody was a horseradish peroxydase-conjugated goat anti-rabbit IgG (Boehringer Mannheim AG, Rotkreuz, Switzerland). Procedures for blotting of the gel onto a nitrocellulose membrane, subsequent incubation with antibodies and detection were as previously described (Viret et al., Infect. Immun. 60 (1992), 2741–2747).

Results, shown in FIG. 5, indicate that most of the clones displayed a LPS pattern identical to that of MO45 (lane 4, characteristic of all O139 strains) in the low size range (lanes 6–11). However, only one clone, namely pSSVI212-3 (lane 5), was identical to the full MO45 LPS pattern, i.e., with both low and high molecular weight material, the latter being typical of capsular polysaccharides. The slight unspecific response from the CH19 carrier strain (lanes 2, 9–11) may be due to some common epitopes in the LPS core of O1 and O139 strains. Since capsular polysaccharides are considered necessary to produce a meaningful immune response against O139 pathogens, pSSVI212-3 was chosen for further work.

Construction of CH25. Further restriction analysis of pSSVI212-3, indicated that no NotI restriction site occurred within the about 30 kb insert. However, NotI sites were available within the cosmid vector pLAFR5 on either side of the insert at 1.0–1.5 kb from the cloning site. Accordingly, the about 32 kb NotI fragment containing the O139 rfb locus was subcloned blunt into the SalI site of integration vector pSSVI209 (FIG. 6) to produce pSSVI220. Plasmid pSSVI220 was then electroporated into *E. coli* S17.1 and mobilized into CH19. The integration procedure of the O139 rfb locus at the hlyA::mer locus was as described in Example 4, except that the presence of the intact O139 rfb locus was checked using the anti-O139 polyclonal antiserum described above which had been preadsorbed against CH19. Several colonies grown at 30° C. without antibiotic selection were found which were $Cm^s$ and reactive with the anti-O139 antibody. One of these colonies was kept and the strain was named CH25.

EXAMPLE 7

Integration of the *S. dysenteriae* rfb/rfp Locus Into the Chromosome of CH19: Construction of Strain CH23

Construction of integration plasmid pSSVI208-2. The source of the rfb/rfp locus from *S. dysenteriae* 1 was plasmid pSS37 (Sturm et al., Microb. Path. 1 (1986), 289–297). The XbaI-EcoRV insert from pSS37 was first cloned in tandem with the Sce-Km cassette (Viret, BioTechniques 14 (1993), 325–326) into the SalI site of the low-copy number vector pGB2 (Churchward et al., Gene 31 (1984), 165–171) to give pSS37-1K. The 13.8 kb insert was then excised with SalI and cloned into the SalI site of the integration vector pSSVI199S (FIG. 7) in both orientations to produce pSSVI208-1K and pSSVI208-2K. The SceI-Km cassette from pSSVI208-2K was then excised by SceI restriction and self-ligation of the plasmid to yield pSSVI208-2 (FIG. 8).

Construction of CH23. Plasmid pSSVI208-2 was electroporated into *E. coli* S17.1, mobilized into CH19, and transconjugants were selected on LB-Cm plates at 30° C. The subsequent integration was as described in Example 4 except that a polyclonal anti-*S. dysenteriae* 1 rabbit antiserum was used for the screening of colonies containing the rfb/rfp locus. Several colonies grown at 30° C. without antibiotic selection were found which were $Cm^s$ and reactive with the anti-*S. dysenteriae* 1 antibody. Qne of these colonies was named CH23.

EXAMPLE 8

Integration of the rfe Gene From *E. coli* Into CH23. Construction of Strain CH24

Rationale for the use of the rfe gene. Previous experimentation had shown that expression of the rfb/rfp locus from *S. dysenteriae* 1 into *V. cholerae* does not result in the production of a complete LPS ladder as seen with the native S. dysenteriae 1 LPS. However, it could be demonstrated that co-expression of the E. coli rfe gene, which encodes the enzyme UDP-N-acetyl-glucosamine::undecaprenylphosphate N-acetylglucosamine-1-phosphate transferase (Meier-Dieter et al., J.Biol.Chem., 267. (1992), 746–753), together with the S. dysenteriae rfb/rfp locus allowed the defect to be overcome, resulting in the production of an LPS ladder indistinguishable from that of S. dysenteriae 1.

Construction of integration plasmid pSSVI219. Accordingly, a plasmid for the integration of the rfe gene into the chromosome of CH23 was constructed. The 1.5 kb XmaIII-ClaI fragment from plasmid pRL100 (Meier-Dieter et al., J.Biol.Chem., 267 (1992), 746–753) was subcloned blunt into the Klenow-blunted BamHI site of plasmid pMAK/hlyA to give pSSVI219 (FIG. 9).

Construction of CH24. Plasmid pSSVI219 was electroporated into *E. coli* S17.1, mobilized into CH23 and transconjugants were selected on LB-Cm plates at 30° C. Subsequent integration procedures were as described in Example 4 except that a *S. dysenteriae* O-PS specific monoclonal antibody (DysH26, unpublished) was used for the screening of colonies with intact rfe gene. The DysH26 mAb specifically recognizes highly polymerized *S. dysenteriae* LPS and therefore discriminates between cells containing an active or an inactive rfe gene. Several colonies grown at 30° C. without antibiotic selection were found which were $Cm^s$ and positive for mAB DysH26. One of these colonies was named CH24.

EXAMPLE 9

Heterolgous O-PS Expression Form Integrated rfb Loci in *V. cholerae* $rfb_{Inaba}$ Mutants Expression of *S. sonnei* rfb/rfc locus alone or in combination with the *E. coli* $rfa_{R1}$locus. The expression of *S. sonnei* and Inaba LPS in CH3 and CH9 and their respective Inaba-negative derivatives was examined on silver-stained SDS-PAGE gels and in immunoblots, using mAb Sh5S (Viret et al., Infect.Immun. 60 (1992), 2741–2747) or VCO4. FIG. 10 depicts the expression of *S. sonnei* and Inaba LPS in the various deletion mutants and their respective parent strains. All $rfb_{Inaba}$ deletions abolished the production of Inaba O-PS (Panels A and C, lanes f to l versus lanes b, d, and e). An unexpected finding was that such deletions also affect the production of the heterologous *S. sonnei* O-PS to various degrees. Strains CH3 and CH9 which harbour an intact $rfb_{inaba}$ locus (lanes d and e, respectively) both expressed limited amounts of core-bound *S. sonnei* O-PS (Panel A). When deletions in genes involved in Inaba O-PS transport/perosamine synthesis or tetronate synthesis were introduced in these strains (CH13/CH14 and CH15, respectively), *S. sonnei* O-PS was poorly expressed and remained unbound (lanes f, g and i of Panel B). In contrast, deletions specific for perosamine synthesis (strains CH21 and CH22) allowed for the expression of large amounts of. core-bound heterologous *S. sonnei* O-PS, depicted as typical LPS ladder-like structures in the lower part of the gel (Panel A and B, lanes k and l).

Expression of *S. dysenteriae* type 1 O-PS in CH23 and CH24. The expression of *S. dysenteriae* LPS in CH23 and CH24 was examined on silver-stained SDS-PAGE gels and in immunoblots using mAb MASD-1 (Fält and Lindberg, Microb.Path. 16 (1994), 27–41) which recognizes both low and high molecular weight *S. dysenteriae* LPS. FIG. 11 clearly shows that the expression of complete LPS depends on the presence of the rfe gene (lanes 2,5,6,8,10). Thus, CH24 (lane 10) produces a LPS ladder which mimics that of the positive controls CH19 and CH3-$I^-$ co-infected with pSSV1208-1 and pRL100 (lanes 5 and 6, respectively) and *E. coli* DH5α (pSS37) (lane 2). In contrast, CH23 (lane 7) synthesizes only a small amount of low molecular weight material. Strains CH23 (pSSV1219) and CH24 (lanes 8 and 10, respectively) synthesized somewhat less highly polymerized LPS than their counterparts bearing the rfb/rfp loci on a plasmid (lanes 5 and 6). Therefore, the difference appears to be due to the lower number of copies of rfb/rfp locus in CH24 versus the strains carrying the plasmid-borne loci.

Expression of *V. cholerae* O139 OA. The expression of *V. cholerae O*139 LPS in CH25 was examined in immunoblots using CH19-adsorbed anti-O139 polyclonal antiserum. FIG. 12 shows that CH25 (lanes 4 and 5) produces both low and high molecular weight LPS typical of O139 wild type strain MO45 (lane 3). Comparison of CH25 LPS to LPS from strains in which the O139 rfb locus is carried on low-copy plasmid vectors in *E. coli* (lanes 6 and 7) indicates that the diminution in copy number resulting -from the chromosomal integration of the O139 rfb locus in CH25 did not result in a corresponding reduction in the amount of LPS produced.

EXAMPLE 10

Physiological Characterization of Carrier Strain CH19 and Candidate Vaccine Strains CH21 and CH22

The physiological properties of the genetically defined $rfb_{Inaba}$ deletion mutants cultured at 30° C. are summarized in Table 2. The phenotype of the deletion mutants was markedly influenced by growth in various media whereas CVD103-HgR was not. When cultivated at 37° C., all strains, including CVD103-HgR showed a drastically reduced motility. The inability of CVD103-HgR to synthesize the Inaba O-PS following the introduction of the rfbAB deletion (strain CH19) resulted in a phenotype which was quite different from the *S. sonnei* O-PS-expressing counterparts, CH21, CH22. Thus, CH19 was poorly motile, grew mostly as single cells or short filaments, and most strikingly, spontaneously aggregated in all media tested. Expression of *S. sonnei* O-PS in the rfbAB deletion background (strain CH22) restored many traits expressed by CVD103-HgR such as motility and growth in non-aggregated, mostly non-filamentous form. Co-expression of the R1 core in strain CH21 resulted in filamentous growth and a diminution of motility.

EXAMPLE 11

Further Physiological Characterization of CH21 and CH22

The stability of both strains was studied. A culture of the test strain was grown to stationary phase at 37° C. in LB medium, diluted 200-fold in the same medium, and further incubated to stationary phase at 37° C. At each round, dilutions of the stationary culture were plated on LB medium for determination of stability. Genetic stability was defined as the proportion of colonies still expressing the desired phenotype (expression of *S. sonnei* O-PS or loss of *V. cholera* O-PS) after 50 or more generations of growth. Both strains were found to stably express (>99.9%) *S. sonnei* O-PS. A similar proportion were found to maintain and express the RI LPS core in strain CH21. On the other hand, all tested colonies failed to express the *V. cholerae* Inaba O-PS.

Strains CH21 and CH22 were also tested for their innocuity by the Y1-adrenal cell assay (Sack and Sack, Infect. Immun. 11 (1975), 334–336), for the production of the cholera toxin B-subunit using the GM1 ganglioside-binding assay (Svennerholm and Holmgren, Curr. Microbiol. 1 (1978), 19–23), and for their resistance to mercury. For the latter test, cultures of CVD103-HgR, CH21 and CH22 were grown overnight with shaking in BHI medium at 37° C. The stationary phase cultures were diluted either 200-fold in 2 ml BHI containing a series of $HgCl_2$ concentrations (BHI/$HgCl_2$) or 40-fold in 20 ml BHI. The latter cultures were further incubated for 2 hours at 37° C. and again diluted 40-fold in 2 ml BHI/$HgCl_2$ medium containing various $HgCl_2$ concentrations. All cultures were then incubated for up to 3 days at 37° C. with shaking. Positive cultures were recorded by visual examination on days 1, 2, and 3. In all three assays, CH21 and CH22 were indistinguishable from CVD103-HgR.

Toxin co-regulated pili, the product of the tcp regulon, is known to be an important factor for V. cholerae adhesion to the intestinal cells. In order to evaluate the expression of tcpA, the gene coding for pilin, Western blots of whole-cell extracts of CVD103-HgR, CH21, and CH22, run on SDS-PAGE gels were probed with a pilin-specific antiserum. Results shown in FIG. 5 indicate that both CH21 and CH22 produce amounts of pilin similar to those of CVD103-HgR.

EXAMPLE 12

Immunogenicity of Strain CH22

Sera from mice immunized with killed whole CH22 cells were tested for the presence of anti-phase I *S. sonnei* and CVD103-HgR Inaba LPS antibodies. As controls, non-immune sera or sera from mice immunized with killed whole CVD103-HgR cells were used. As shown in Table 3, immunization with CH22 induced high titers of anti-*S. sonnei* LPS antibodies but no anti-Inaba LPS antibodies. In contrast, sera from mice immunized with CVD103-HgR produced only anti-Inaba LPS antibodies. Sera from control mice did not react with any of the LPS test antigens.

Legends to the Figures

FIG. 1: Restriction map of the Inaba rfb clone pSSVI255-7 and derived deletion vectors.

The arrows depict the direction of transcription of the rfaD gene and $rfb_{Inaba}$ operon. The white boxes delineate the various rfb genes and the striped boxes denote functional regions. These data are inferred from published results (Manning, P. A., et al. p. 77–94. In Vibrio cholerae and Cholera: molecular to global perspectives. Wachsmuth K., Blake, P. A., and Olsvik φ. (eds.). Washington, D.C.:American. Society for Microbiology, 1994. The lines below correspond to plasmid inserts indicated on the right. The portions with a thick double line represent homologous regions used for chromosomal integration and excision of vector sequences. The remaining portions (thin lines) represent the chromosomal regions deleted from each plasmid.

Figure 2:
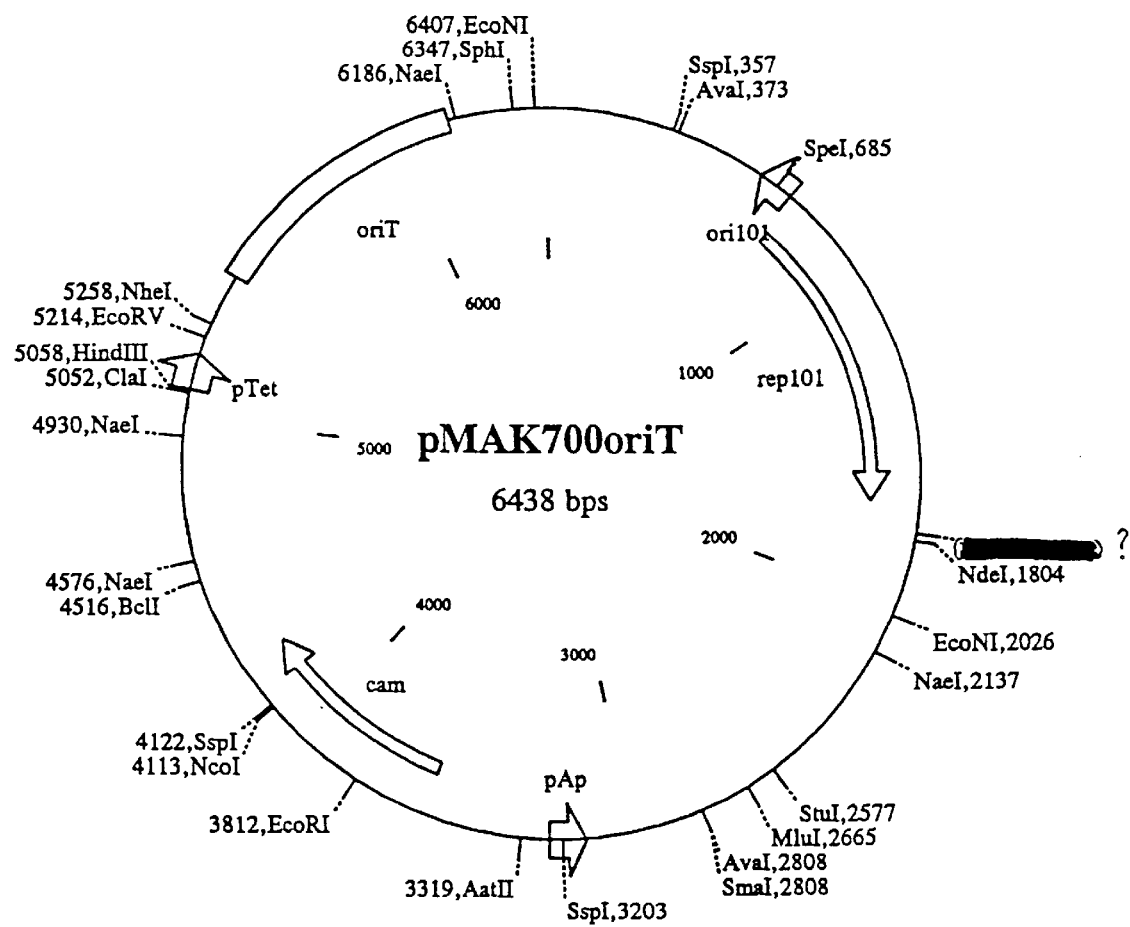

FIG. 2: Restriction map of the mobilizable suicide vector pMAX700oriT.

ori101, pSC101 origin of replication; rep101, gene for the temperature-sensitive replication initiation protein; cam, chloramphenicol resistance gene; oriT, RP4/RK2 origin of transfer. Coordinates are in base pairs.

Figure 3:
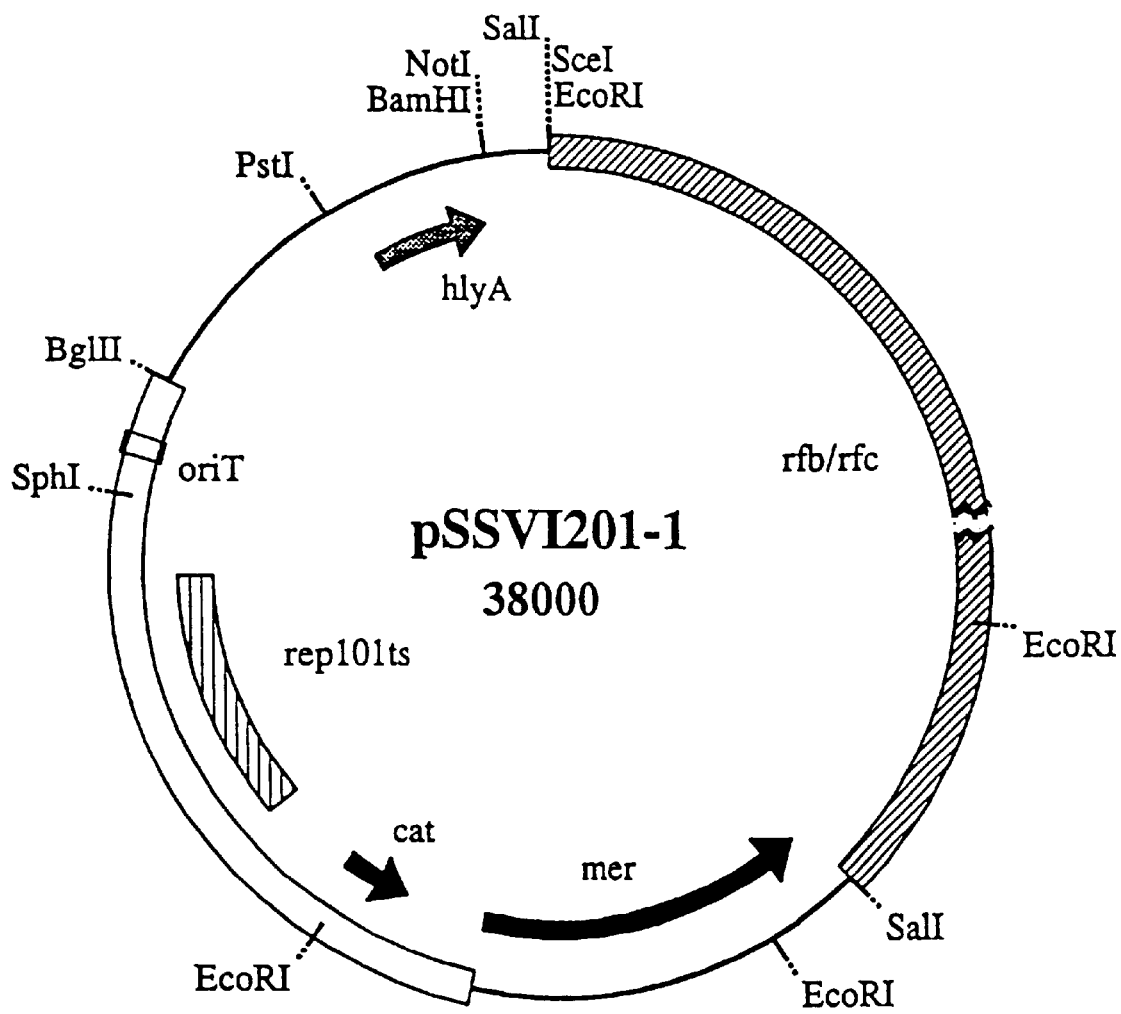
Figure 4:
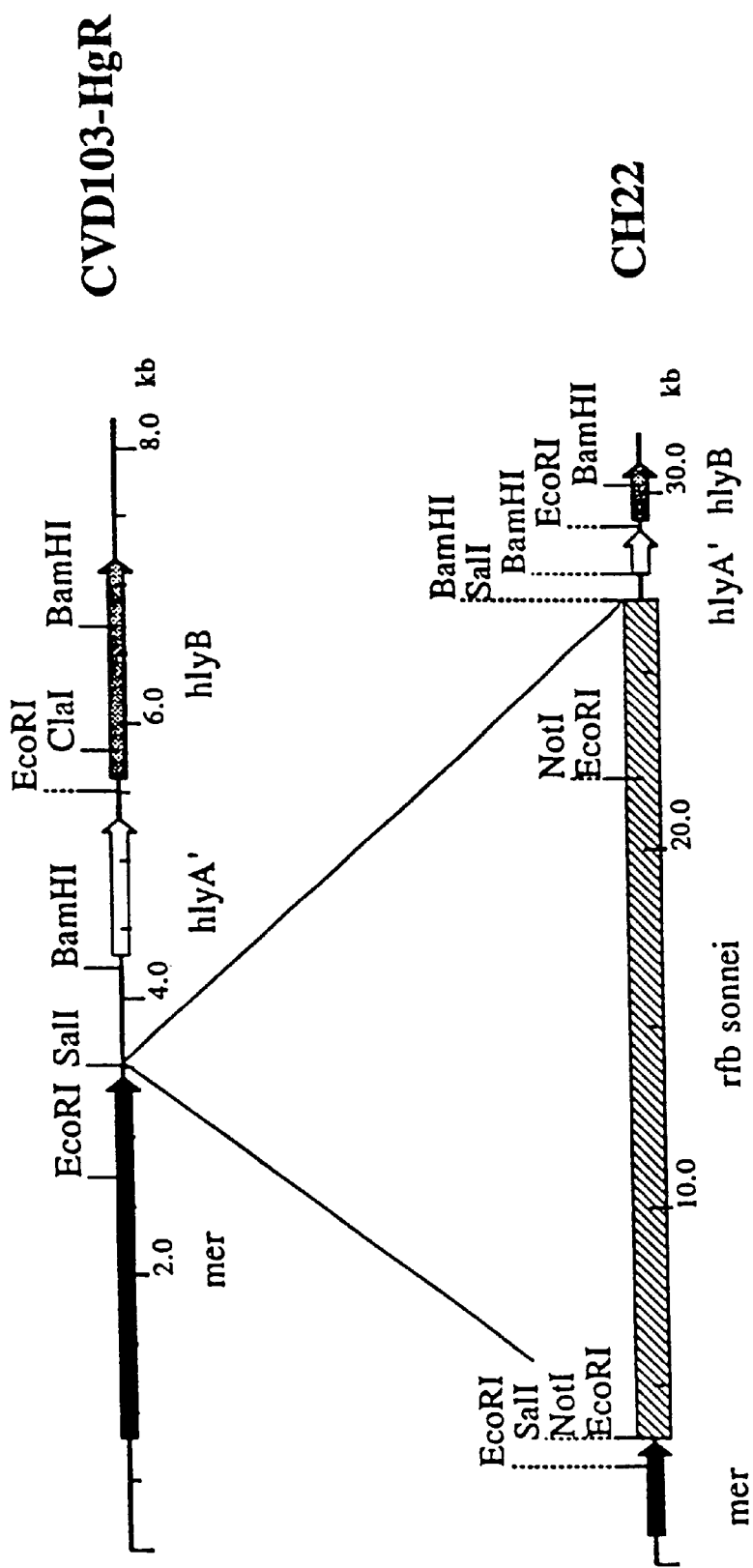

FIG. 3: Restriction map of $rfb/rfc_{sonnei}$ locus intgration plasmid pSSVI201-1.

The arrows depict the direction of transcription of the indicated genes. The white box represents the pMAK700oriT vector. The interrupted striped box on the map line represents the *S. sonnei* rfb/rfc locus. The interruption denotes that its actual size is larger than represented. The thin lines are the regions homologous to CVD103-HgR chromosomal DNA. hlyA, 5'-end of the hlyA gene; mer, mercury resistance operon; cat, chloramphenicol resistance gene; rep101ts, gene for the temperature-sensitive replication initiation protein; oriT, RP4/RK2 origin of transfer.

FIG. 4: Genetic structure of CH22 at the hlyA::$rfb_{sonnei}$ locus.

The upper map depicts the structure of the hlyA:mer locus in CH19, i.e., before integration of the $rfb_{sonnei}$ region in the SalI site. Arrows denote the direction of transcription of the indicated genes.

Figure 5A:
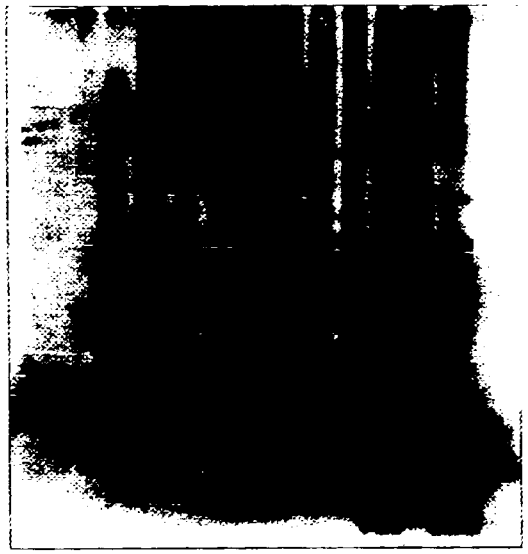
Figure 5B:

FIGS. 5A and 5B SDS-Page analysis of LPS minipreparations of O139 rfb clones in *E. coli* HB101 and *V. cholerae* CH19.

Panel A: silver stained. Panel B: Western blot using CH19-adsorbed polyclonal rabbit O139-specific antiserum. Lanes: 1, Molecular weight markers; 2, CH19; 3, HB101 (pSSVI212-15) negative control; 4, MO45 positive control; 5, HB101 (pSSVI212-3); 6, HB101 (pSSVI212-10); 7, HB101 (pSSVI212-13); 8, HB 101 (pSSVI212-16); 9, CH19 (pSSVI212-10); 10, CH19 (pSSVI212-13); 11, CH19 (pSSVI212-16)

Figure 6:
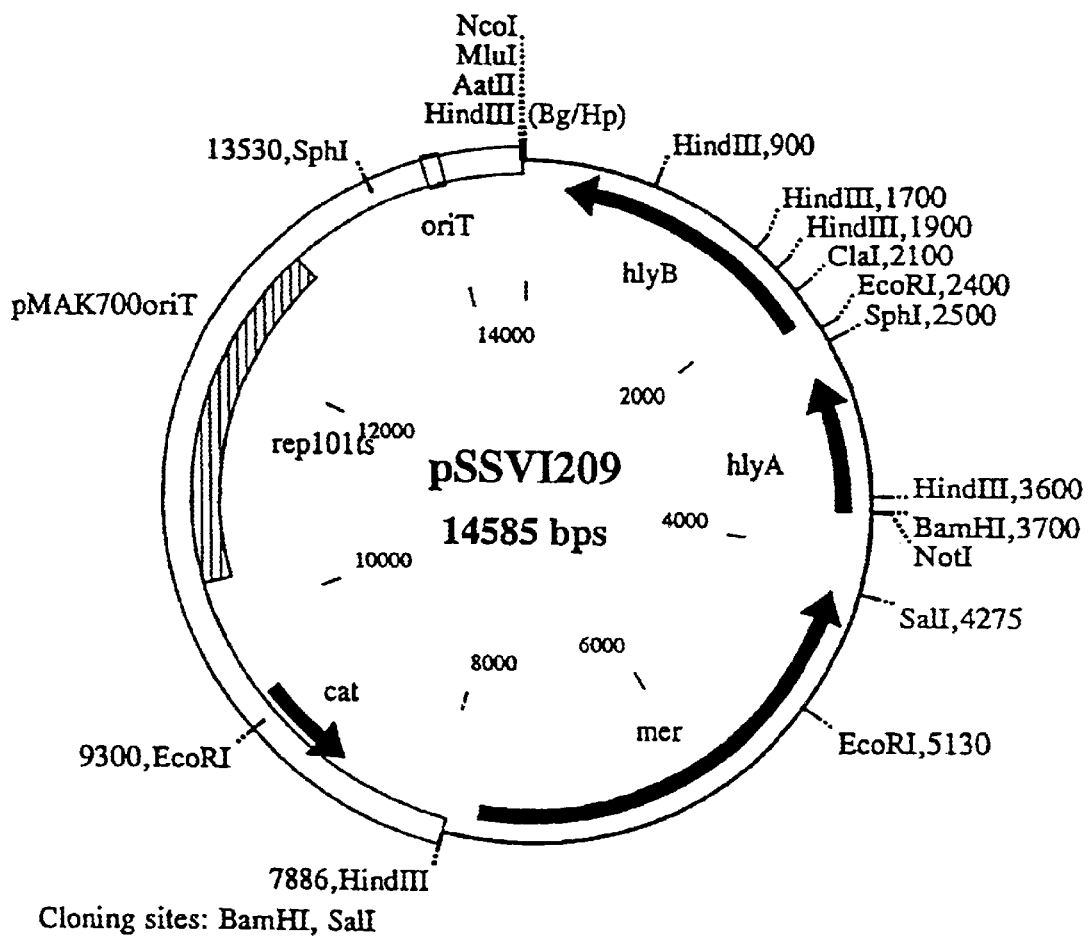

FIG. 6: Restriction map of the integration vector pSSVI209.

Figure 7:
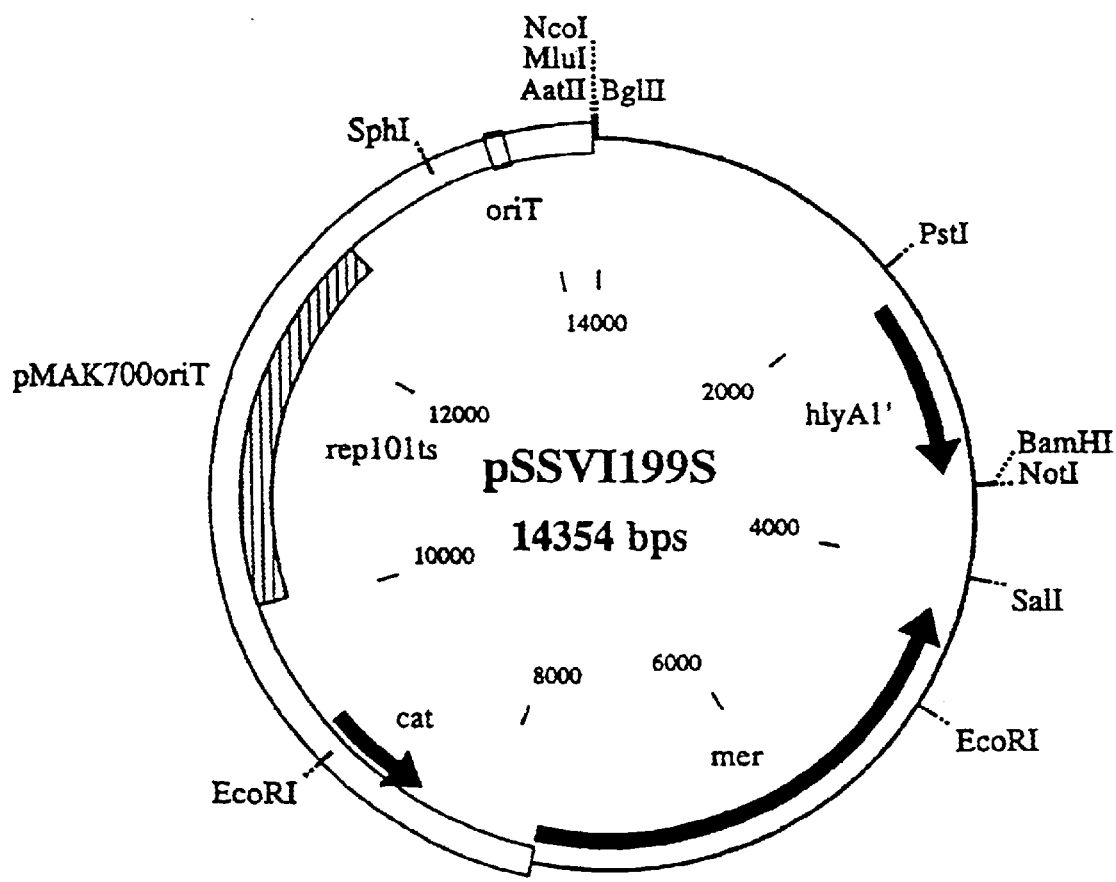

Abbreviations and symbols are as in FIG. 3;

FIG. 7: Restriction map of the integration vector pSSVI199S.

Abbreviations and symbols are as in FIG. 3.

Figure 8:
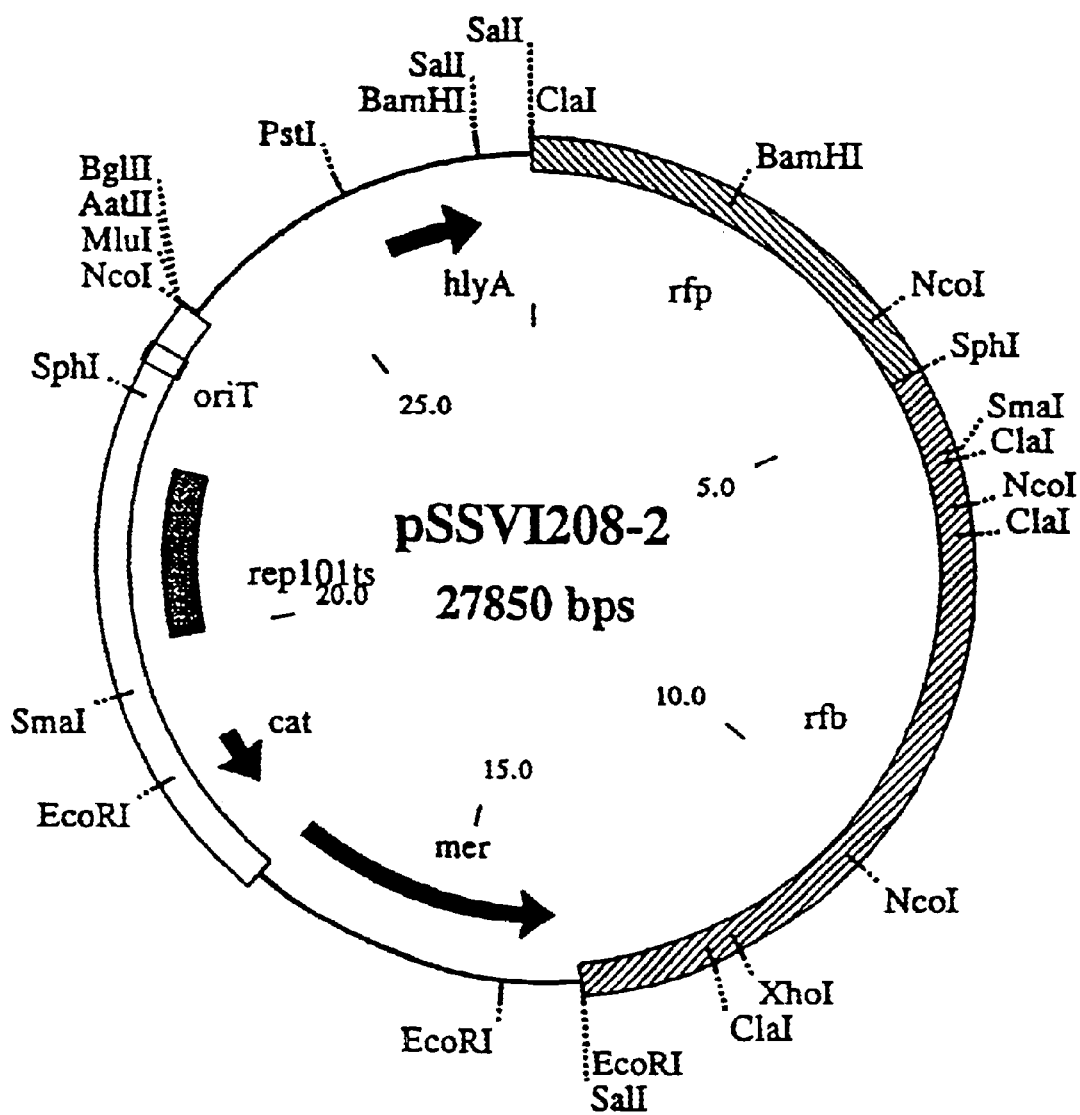

FIG. 8: Restriction map of the *S. dysenteriae* rfb/rfp loci integration plasmid pSSVI208-2.

Abbreviations and symbols are as in FIG. 3. Box with: left stripes, rfp locus; right stripes, rfb locus.

Figure 9:
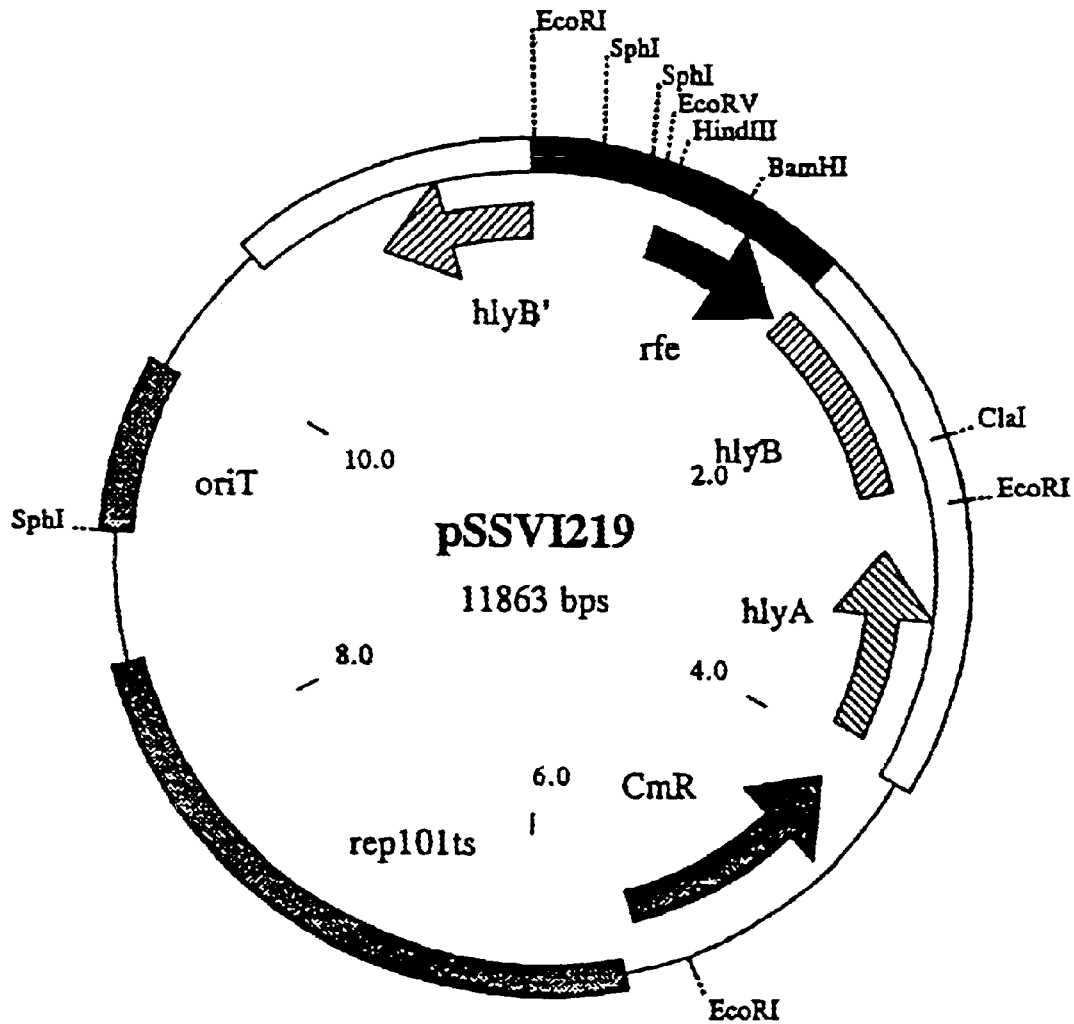

FIG. 9: Restriction map of the *E. coli* rfe gene integration plasmid pSSV1219.

The arrows depict the direction of transcription of the indicated genes. White boxes: region homologous to CVD103-HgR genome; black box, rfe gene; thin line+dotted boxes, pMAK700oriT vector. CmR, chloramphenicol resistance gene hlyB, 5' end of the disrupted hlyB gene; hlyB', 3' end of the disrupted hlyB gene. Otherwise, as in FIG. 3.

Figure 10C:
Figure 10B:
Figure 10A:
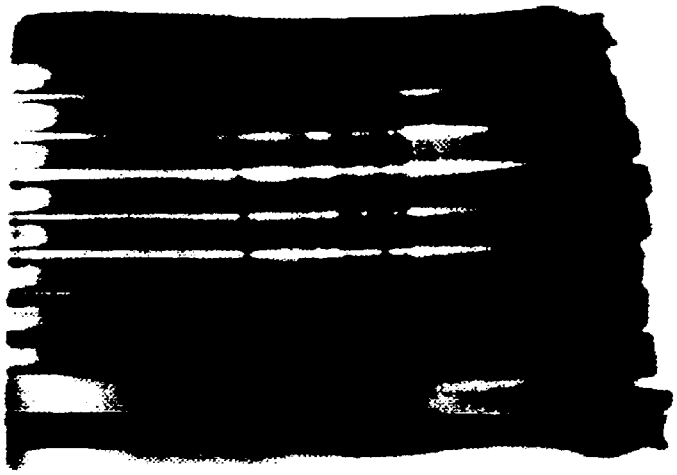

FIGS. 10A–10C: SDS-PAGE analysis of O-PS expression in various $rfb_{Inaba}$ mutants of CVD103-HgR, CH3, and CH9, and in CH22.

Panels: A, silver stained gel; B, immunoblot with *S. sonnei*-specific MAb Sh5S; C, immunoblot with the *V. cholerae* O-PS-specific MAb VCO4. Lanes: a, Molecular weight standard; b, CVD103-HgR; c, *S. sonnei* 482–79 (pWR105); d, CH3; e, CH9; f, CH13; g, CH14; h, CH15; i, CH17; j, CH19; k, CH21; 1, CH22.

Figure 11:
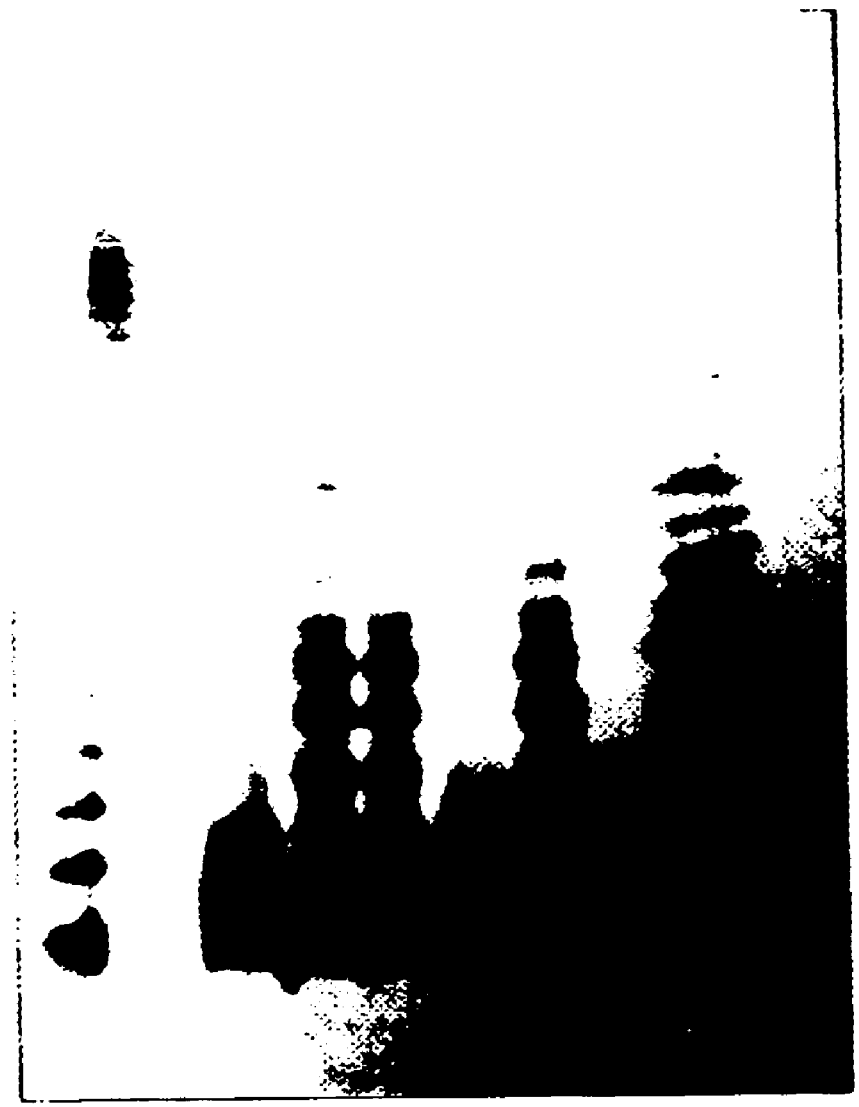

FIG. 11: Western blot analysis of LPS minipreparations of CH23, CH24, and *V. cholerae* carrier strains with plasmid-borne rfb/rfp loci alone or together with the plasmid-borne rfe gene.

Lanes: 1, molecular weight markers; 2, DH5α (pSS37); 3, CH19; 4, CH19 (pSSVI208-2); 5, CH19 (pSSVI208-2/pRL100); 6, CVD-I⁻ (pSSVI208-2/pRL100); 7, CH23; 8, CH23 (pSSVI219); 9, CH23 (pRL100), 10, CH24. Probing antibody: mouse *S. dysenteriae* O-PS-specific MAb MASD-1.

Figure 12:
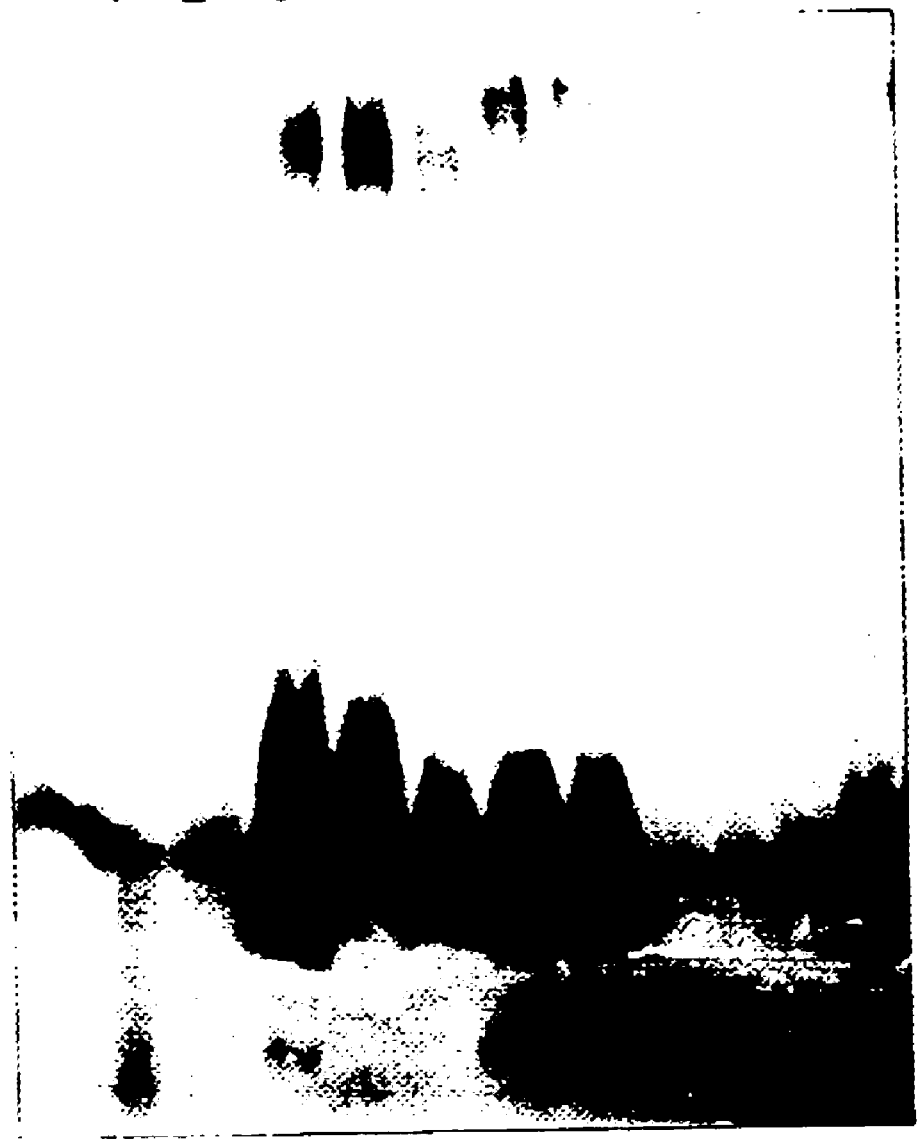

FIG. 12: Western blot analysis of LPS minipreparations of O139 rfb clones in *E. coli* HB101 and *V. cholerae* CH25.

Lanes: 1, Molecular weight markers; 2, HB101 (pSSVI215) negative control; 3, MO45 positive control; 4 and 5, CH25; 6, HB101 (pSSVI215-$1_2$); 7, HB101 (pSSVI215-$2_3$). Probing antibody: CH19-adsorbed polyclonal rabbit O139-specific antiserum.

Figure 13:
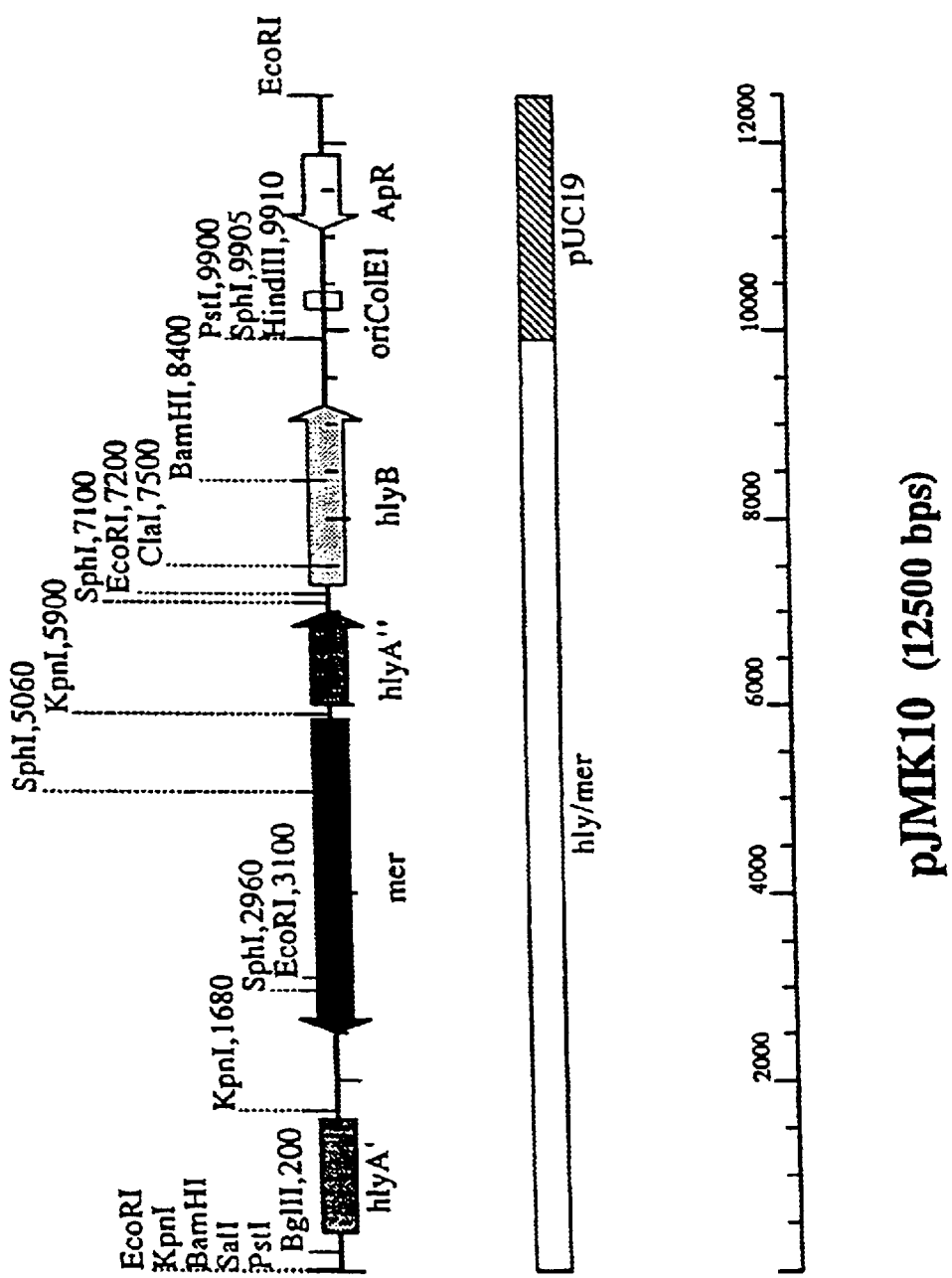

FIG. 13: Restriction map of plasmid pJMK10.

TABLE 1

Strains and plasmids

| Strains and plasmids | Genotype/Description[a] | Source |
|---|---|---|
| Strains | | |
| *E.coli* | | |
| HB101 | supE44 ara14 galK2 lacY1 proA2 rpsL20 xyl-5 mtl-1 recA13 Δ(mcrC-mrr) | Sambrook et al. Molecular cloning, 2nd edition, Cold Spring Harbor Laboratory Press, Cold Spring Harbor USA, (1989) |
| DH5α | F-Φ80dlacZΔM15 Δ(lacZYA-argF) U169 deo recA1 endA1 hsdR17 (rK−,mK+) supE44 λ- thi1 gyrA96 relA1 phoA | Sambrook et al. Molecular cloning, 2nd edition, Cold Spring Harbor Laboratory Press, Cold Spring Harbor USA, (1989) |
| S17.1 | thi-1 pro hsdR Tp$^r$ Sm$^r$ RP4-2[Tc::Mu(Km::Tn7)] | Simon et al. Bio/Technology 1 (1983), :784 |
| *S.sonnei* | | |
| 482-79 (pWR105) | Phase I (smooth LPS) | Sansonetti et al., Infect. Immun., 34 (1981), 75 |
| *V.cholerae* | | |
| CVD103-HgR | O1 Classical Inaba. ΔctxA hlyA::mer (Hg$^R$) | Ketley et al., FEMS Microbiol. Lett. 111 (1993), 15 |
| CVD111 | O1 El Tor Ogawa. Δ(ctxA zot ace) hlyA::(ctxB mer) (Hg$^R$) | M. M. Levine, pers. communication |
| M045 | wild type O139. Reference epidemic strain | Madras, India |
| CH3 | ΔctxA hlyA::mer hlyA::rfb/rfc$_{sonnei}$ | Viret and Favre, Biologicals 22 (1994), 361 |
| CH9 | ΔctxA hlyA::mer hlyA::rfb/rfc$_{sonnei}$hlyB::rfa$_{R1}$ | Viret and Favre, Biologicals 22 (1994), 361 |
| CH13 | CH3 ΔrfbDEGHI | Present invention |
| CH14 | CH9 ΔrfbDEGHI | Present invention |
| CH15 | CVD103-HgR ΔrfbN | Present invention |
| CH17 | CH9 ΔrfbN | Present invention |
| CH19 | CVD103-HgR ΔrfbAB | Present invention |
| CH21 | CH9 ΔrfbAB | Present invention |
| CH22 | CH19 hlyA::rfb/rfc$_{sonnei}$ | Present invention |
| CH23 | CH19 hlyA::rfb$_{dysenteriae}$ | Present invention |
| CH24 | CH19 hlyA::rfb$_{dysenteriae}$hlyA::rfe | Present invention |
| CH25 | CH19 hlyA::rfb$_{O139}$ | Present invention |
| CH30 | CVD111 ΔrfbAB | Present invention |
| Plasmids | | |
| pLAFR5 | Broad host range cosmid vector 21.5 kb | Keen et al., Gene 70 (1988),.191 |
| PMTL22p | high-copy number general purpose plasmid vector | Chambers et al., Gene 68 (1988), 139 |
| pMAK700 | low-copy number thermosensitive suicide vector | Hamilton et al., J. Bacteriol. 171 (1989), 4617 |
| pJFF350 | transposon delivery vector with oriT sequence | Fellay et al., Gene 76 (1989), 215 |
| pGB2 | low copy number general purpose cloning vector | Churchward et al., Gene 31 (1984), 165 |
| pSSVI186-1 | Plasmid pUC21 carrying the Sce-Km cassette | Viret, BioTechniques, 14 (1993), 325 |
| pSS37 | pACYC184 carrying the rfb and rfp loci of *S.dysenteriae* 1 | Sturm et al. Microb. path. 1 (1986), 289 |
| pRL100 | plasmid bearing the rfe gene from *E. coli* | Meier-Dieter et al., J. Biol. Chem., 267 (1992), 746 |
| pJMK10[b] | pUC19 carrying a 9.9 kb fragment with the hlyA-hlyB region from *V.cholerae* 569B (wild type) interrupted by a 4.22 kb fragment bearing the mer operon (mercury resistance genes) | Ketley et al., FEMS Microbiol. Lett. 111 (1993), 15 |
| pMAK700oriT | Mobilizable suicide vector. pMAK700 with 0.75 kb oriT EcoRI-BamHI fragment from pJFF350 | Present invention |
| pSSVI255-3 | rfb$_{Inaba}$ locus cloned into pLAFR5 | Present invention |
| pSSVI255-5 | rfb$_{Inaba}$ locus cloned into pLAFR5 | Present invention |
| pSSVI255-7 | rfb$_{Inaba}$ locus cloned into pLAFR5 | Present invention |
| PSSVI205-1 | pMAK700oriT carrying the entire insert of pSSVI255-7 from which the three internal SacI fragments were deleted. The insert contains also, ca., 1 kb of pLAFR5 DNA | Present invention |
| PSSVI205-2 | same as pSSVI205-1 but insert in opposite orientation | Present invention |
| pSSVI255-12 | PMAK700oriT carrying the HindIII-SalI fragment of pSSVI255-7 at coordinates 8420-11730 from which the central BamHI fragment was deleted | Present invention |
| pSSVI255-19 | pMAK700oriT carrying the ClaI fragment from pSSVI255-7 at coordinates 15770-21030 from which the central SalI fragment was deleted | Present invention |
| pSSVI255-20 | pMAK700oriT carrying the SacI-BamHI fragment from pSSV1255-7 at coordinates 5000-10340 from which the central HindIII fragment was deleted | Present invention |
| pSSVI199S | pMAK700oriT carrying the hlyA::mer locus, coordinates 0-5900 from plasmid pJMK10, added with a 2kb PCR fragment adjacent to the 5'-end of hlyA. An extra SalI cloning site was created 345 bp downstream of merA | Present invention |

TABLE 1-continued

Strains and plasmids

| Strains and plasmids | Genotype/Description[a] | Source |
|---|---|---|
| pSSVI201-1 | pSSVI199S carrying the the rfb/rfc$_{sonnei}$ locus | Present invention |
| pSSVI212-13 | pLAFR5 with the O139 rfb locus from *V.cholerae* O139 strain MO45 | Present invention |
| pSSVI209 | pMAK700oriT carrying the hlyA"-hlyB fragment from pJMK10 (coordinates 5900-9900) completed with the mer cassette (pJMK10 coordinates 1680-5900) in reverse orientation | Present invention |
| pSSVI220 | pSSVI209 with the NotI fragment from pSSVI212-3 cloned blunt into the SalI site | Present invention |
| pSS37-1K | pGB2 with the XbaI-EcoRV 13.5 kb fragment from pSS37 carrying the rfb/rfp loci of *S.dysenteriae* 1 cloned blunt together with the Sce-Km cassette from plasmid pSSVI186-1 | Present invention |
| pSSVI208-1K | pSSVI199S carrying the rfb/rfp loci from *S. dysenteriae* together with the Sce-Km cassette from pSSVI186-1 | Present invention |
| pSSVI208-2K | Same as pSSVI208-1K but rfb/rfp loci from *S. dysenteriae* and Sce-Km cassette in reverse orientation | Present invention |
| pSSVI208-2 | pSSVI208-2K from which the Sce-Km cassette was excised | Present invention |
| pMAK/hlyA | pMAK700 oriT bearing the hlyA"-hlyB fragment from pJMK10 (coordinates 5900-9900) | Present invention |
| pSSVI219 | pMAK/HlyA bearing the XmaI-ClaI fragment from pRL100 containing the rfe gene from *E. coli* | Present invention |

[a]Coordinates for pSSVI255-7 are given in FIG. 1.
[b]Coordinates for pJMK10 are given in FIG. 13.

TABLE 2

Phenotypic characterization of CVD103-HgR and Inaba LPS mutants

| | | | | cellular phenotype | | |
|---|---|---|---|---|---|---|
| Strain | affected function | medium[a] | Motility[b,e] | single cells[e] | filaments[e] | aggregates[d,e] |
| CVD103-HgR | None | CF | +++ | +++ | − | − |
| | | LB | +++ | +++ | − | − |
| | | BHI | ++ | +++ | − | − |
| CH13 | O–antigen transport, synthesis | CF | − | ++ | ++ | − |
| | | LB | + | +++ | + | + |
| | | BHI | − | ++ | + | + |
| CH14 | O–antigen transport, synthesis | CF | − | ++ | +++ | − |
| | | LB | + | ++ | +++ | + |
| | | BHI | − | + | +++[c] | − |
| CH15 | perosamine modification | CF | − | ++ | +++ | +++ |
| | | LB | + | + | + | +++ |
| | | BHI | + | ++ | +++ | ++ |
| CH17 | perosamine modification | CF | − | + | +++[c] | − |
| | | LB | ++ | + | +++ | + |
| | | BHI | + | ++ | +++[c] | − |
| CH19 | perosamine synthesis | CF | − | +++[f] | + | +++ |
| | | LB | + | +++ | − | +++ |
| | | BHI | + | +++ | − | +++ |
| CH21 | perosamine synthesis | CF | − | ++ | +++[c] | − |
| | | LB | + | ++ | +++ | − |
| | | BHI | − | + | +++[c] | − |
| CH22 | perosamine synthesis | CF | ++ | ++ | ++ | − |
| | | LB | +++ | +++ | + | − |
| | | BHI | + | +++ | ++ | − |

[a]The strains were grown to stationary phase at 30° C. in the indicated medium
[b]Microscopically determined.
[c]Most filaments consisted of ≧10 cells
[d]Large clusters of adherent cells
[e]
− not present
+ present in 1 to 20% of population
++ present in 20 to 60% of population
+++ present in 60 to 100% of population

TABLE 3

Antibody response following immunization with *V. cholerae* strains CH22 or CVD103-HgR.

| Immunizing strain[a] | Geometric mean antibody titers[b] | |
|---|---|---|
| | *S. sonnei* phase 1 LPS | *V. cholerae* Inaba LPS |
| NONE | <10 | <10 |
| CH2 | 3'313 | <14 |
| | (650–10'200) | (<10–71) |
| CVD103-HgR | <10 | 260 |
| | | (57–730) |

[a]Groups of seven mice were immunized intramuscularly (IM) at days 0 and 14 with 5 × 10[7] heat inactivated cell. A booster dose was given intraperitoneally on day 21. Control mice were not immunized. All mice were sacrificed on day 28.
[b]Sera were tested individually for LPS-specific antibodies using purified *S. sonnei* phase 1 or *V. cholerae* Inaba as coating antigens in an ELISA assay. Titers are expressed as the geometric mean (range) of the reciprocals of the highest dilution resulting in an $OD_{405\ nm}$ of 0.4.

What is claimed is:

1. A live attenuated vaccine strain selected from the group consisting of *Escherichia coli, Salmonella typhi, Vibro cholerae* and Shigella, wherein said strain is unable to express homologous O-polysaccharide due to the introduction, by recombinant techniques, of a 1.2 kb deletion that spans the junction of the rfbA and rfbB genes, and expresses at least one heterologous O-polysaccharide gene in such a way that said heterologous gene expresses a heterologous O-polysaccharide that is covalently linked to a lipopolysaccharide core.

2. The live attenuated vaccine strain according to claim 1, wherein said 1.2 kb deletion is a HinDIII deletion.

3. The live attenuated strain according to claim 1, wherein said heterologous O-polysaccharide gene is integrated into a chromosomal locus selected from the group consisting of hlyA, hlyB ctxA, rfbA, rfbB, and rfbA and rfb.

4. The live attenuated vaccine strain according to claim 1, wherein said strain is combined with a pharmaceutically acceptable carrier.

5. The live attenuated vaccine strain according to claim 1, wherein said strain is combined with a buffer for neutralizing gastric acidity.

6. The vaccine strain of claim 1, wherein said heterologous O-polysaccharide gene is present on a plasmid vector or stably integrated into the chromosome of said strain at a defined integration site which is non-essential for inducing a protective immune response by the carrier strain, said defined integration site being a homologous genetic region corresponding to the genetic region flanking said heterologous O-polysaccharide gene.

7. The vaccine strain of claim 6, wherein said heterologous O-polysaccharide gene is integrated into a chromosomal locus selected from the group consisting of hlyA, hlyB, ctxA, rfbA, rfbB, and rfbA and rfbB.

8. The vaccine strain of claim 6, wherein the strain is a *S. typhi* strain and wherein said heterologous O-polysaccharide gene is integrated into a gene selected from the group consisting of the $H_2S$ production gene, ilv, viaB, and htpR genes involved in virulence traits and genes involved in the synthesis of aromatic acids.

9. The vaccine strain according to any one of claims 6 or 7, wherein rfa, rfe, and rfp genes are integrated in tandem into a single chromosomal site or independently integrated into individual sites.

10. The strain according to claim 9, wherein the rfa genes encode the Ra, R1, R2, R3, R4, K-12 or B LPS core.

11. The strain according to claim 9, wherein the rfa genes encode the R1 core.

12. The live attenuated vaccine strain which is *Vibrio cholerae* CH21, identified by the accession number DSM13421.

13. The *Vibrio cholerae* vaccine carrier strain, CH19, identified by the accession number DSM13420.

14. A live attenuated vaccine comprising the vaccine strain of claim 12, wherein said strain is combined with a pharmaceutically acceptable carrier.

15. A live attenuated vaccine comprising the vaccine strain of claim 12, wherein said strain is combined with a buffer for neutralizing gastric acidity.

16. A live attenuated vaccine comprising the vaccine strain of claim 12, wherein said vaccine is delivered in a viable state to the intestinal tract.

17. The live attenuated vaccine of claim 12 for immunization of a mammalian subject in need thereof against a gram-negative enteric pathogen selected from the group consisting of *Shigella sonnei* and *Vibrio cholerae*.

18. The live attenuated vaccine of claim 12 for oral or intranasal administration.

19. The live attenuated vaccine strain according to claim 1, wherein said *V. cholerae* strain is selected from the group consisting of O1 *V. cholerae* and O139 *V. cholerae*.

20. The live attenuated vaccine strain according to claim 1, wherein said *V. cholerae* strain is O139 *V. cholerae* selected from the group consisting of CVD112 and Bengal-15, or O1 *V. cholerae* selected from the group consisting of CVD103, CVD103-HgR, CVD110, CVD111 and Peru-14.

21. The vaccine strain of claim 1, wherein said heterologous O-polysaccharide gene is integrated into a chromosomal locus selected from the group consisting of hlyA, hlyB and ctxA.

22. A method for immunizing against a gram-negative enteric pathogen selected from the group consisting of *Shigella sonnei* and *Vibrio cholerae* comprising administering the vaccine strain of claim 12.

23. A method for immunization against an enteric infection caused by a gram negative bacterial pathogen selected from the group consisting of *Escherichia coli, Salmonella typhi, Vibrio cholerae* and Shigella comprising administering the live attenuated vaccine strain of claim 1, wherein said vaccine strain expresses the heterologous O-polysaccharide of the corresponding said bacterial pathogen.

* * * * *